United States Patent
Massey et al.

(10) Patent No.: US 11,497,824 B2
(45) Date of Patent: Nov. 15, 2022

(54) UV DISINFECTANT SYSTEM

(71) Applicant: SAFE FOODS CORPORATION, North Little Rock, AR (US)

(72) Inventors: Justin Massey, North Little Rock, AR (US); Tim Yeaman, North Little Rock, AR (US)

(73) Assignee: SAFE FOODS CORPORATION, North Little Rock, AR (US)

( * ) Notice: Subject to any disclaimer, the term of this patent is extended or adjusted under 35 U.S.C. 154(b) by 775 days.

(21) Appl. No.: 16/095,715

(22) PCT Filed: Apr. 25, 2016

(86) PCT No.: PCT/US2016/029114
§ 371 (c)(1),
(2) Date: Oct. 23, 2018

(87) PCT Pub. No.: WO2017/188915
PCT Pub. Date: Nov. 2, 2017

(65) Prior Publication Data
US 2020/0330629 A1    Oct. 22, 2020

(51) Int. Cl.
*A61L 2/10* (2006.01)
*A61L 2/24* (2006.01)
(Continued)

(52) U.S. Cl.
CPC .................. *A61L 2/10* (2013.01); *A61L 2/24* (2013.01); *B01F 25/43151* (2022.01);
(Continued)

(58) Field of Classification Search
None
See application file for complete search history.

(56) References Cited

U.S. PATENT DOCUMENTS

2001/0027168 A1* 10/2001 Adams ................ B01F 13/1041
                                                              507/117
2003/0021089 A1*  1/2003 Belady ................... F04D 29/38
                                                              361/695
(Continued)

FOREIGN PATENT DOCUMENTS

CN       203821125 U  *  9/2014
CN       203821127 U  *  9/2014

OTHER PUBLICATIONS

International Search Report and Written Opinion issued by the United States Patent and Trademark Office as International Searching Authority for PCT/US2016/029114, dated Jul. 27, 2016, 11 pgs.

*Primary Examiner* — Andrew Smyth
(74) *Attorney, Agent, or Firm* — Haynes and Boone, LLP

(57) ABSTRACT

A UV disinfectant system may include a chamber having a wall that is transparent to a disinfecting radiation. Liquid may be flowed through the chamber for treatment by exposure to the radiation. The chamber may include a static mixer having vanes to impede laminar flow of the liquid during treatment. The vanes extend into the flow path of the liquid through the chamber. A gap is defined between the vanes and the transparent wall. A cabinet may house the chamber and radiation emitting bulbs. Blowers may be operably coupled to a temperature sensor and flow meter and positioned at a lower end and upper end of the cabinet to urge air out of the cabinet. The temperature sensor may include a thermocouple. The blowers may be variable speed blowers. The system may include a controller to control system operations. The controller may be remotely accessible to monitor or control operations.

10 Claims, 11 Drawing Sheets

(51) Int. Cl.
  *C02F 1/00*      (2006.01)
  *C02F 1/32*      (2006.01)
  *B01F 25/431*    (2022.01)
  *A23L 2/50*      (2006.01)
  *A23L 3/28*      (2006.01)
  *B01F 101/00*    (2022.01)

(52) U.S. Cl.
  CPC .............. *C02F 1/008* (2013.01); *C02F 1/325* (2013.01); *A23L 2/50* (2013.01); *A23L 3/28* (2013.01); *A23V 2002/00* (2013.01); *A61L 2202/11* (2013.01); *A61L 2202/122* (2013.01); *A61L 2202/14* (2013.01); *B01F 2101/305* (2022.01); *C02F 2201/326* (2013.01); *C02F 2201/328* (2013.01); *C02F 2201/3227* (2013.01); *C02F 2201/3228* (2013.01); *C02F 2209/005* (2013.01); *C02F 2209/02* (2013.01); *C02F 2209/40* (2013.01); *C02F 2301/024* (2013.01); *C02F 2303/04* (2013.01)

(56) References Cited

U.S. PATENT DOCUMENTS

| | | | | |
|---|---|---|---|---|
| 2008/0095661 | A1* | 4/2008 | Kohler | C02F 1/487 422/119 |
| 2008/0224066 | A1* | 9/2008 | Nolen | A61L 2/10 250/436 |
| 2010/0326114 | A1* | 12/2010 | Kim | F25D 23/028 210/139 |
| 2011/0186495 | A1* | 8/2011 | Robinson | C02F 1/006 210/198.1 |
| 2011/0260077 | A1* | 10/2011 | Boschert | A01K 7/02 250/432 R |

* cited by examiner

UV DISINFECTANT SYSTEM

TECHNOLOGY

The present disclosure relates to disinfectant systems and control and monitoring of disinfectant systems.

BACKGROUND

UV radiation may be used to disinfect clear or opaque liquids such as water, including wastewater, juices, brines, marinades, beverages, and the like. Examples include U.S. Pat. Nos. 3,527,940 and 4,968,891 and U.S. patent application Ser. No. 10/542,793, the disclosures of which are incorporated herein by reference. Using UV radiation to disinfect liquids offers many advantages that often make it a very attractive option as compared to other methods of disinfecting liquids. It will often provide for improved disinfection in a fast, simple, relatively inexpensive manner.

The effectiveness of UV radiation to disinfect a liquid diminishes rapidly with the distance that the radiation must pass through the liquid, so the surface of the liquid receives stronger radiation than the depths of the liquid. So under conditions of laminar flow, disinfection of the deeper liquid is less than disinfection of the surface of the liquid. Furthermore, relying primarily upon natural turbulence in a liquid to provide for even, thorough disinfection of the liquid can be unreliable.

SUMMARY

In one embodiment, a UV disinfectant system comprises a chamber and a plurality of ultraviolet light emitting bulbs. The chamber may have at least one wall transparent to ultraviolet light and define a treatment flow path for liquid to be treated with the ultraviolet light. The plurality of ultraviolet light emitting bulbs may be positioned external to the chamber, adjacent to the transparent wall to direct ultraviolet light into the chamber along the treatment flow path. The system may further include an inflow port, outflow port, and pump. The inflow port may be configured for passage of the liquid to be treated into the treatment flow path. The outflow port may be configured for passage of the treated liquid from the treatment flow path to an outlet of the chamber. The pump may be configured for pumping the liquid through the chamber. The system may further include a static mixer positioned in the chamber and comprising a plurality of vanes extending into the treatment flow path, dimensioned to disrupt laminar flow along the treatment flow path. The treatment flow path may include a gap passing between at least one of the vanes and the transparent wall. The system may further include a cabinet housing the chamber and bulbs and having an upper end and a lower end. A first blower may be positioned to drive airflow out of the cabinet at the lower end. A second blower may be positioned to drive airflow out of the cabinet at the upper end. A vent may enable airflow into the cabinet between the upper end and the lower end of the cabinet. An air temperature sensor may be configured to measure air temperature at one or more locations within the cabinet. A liquid temperature sensor may be configured to measure a liquid temperature at one or more locations within the chamber. A flow meter may be configured to measure a flow rate of liquid at one or more locations within the chamber. The system may further include a controller operable to control operations of the pump, bulbs, and blowers and operationally coupled to the air temperature sensor, liquid temperature sensor, and flow meter to receive collected measurement data. The controller comprises a processor, a computer-readable storage medium having instructions stored executable by the processor to perform the operations of the UV disinfectant system, and a user interface operable to interface users with the controller to view measurement data collected from the air temperature sensor, liquid temperature sensor, and flow meter and to modify at least one of power delivery to the bulbs, blower speed, or pump speed.

In another aspect, a UV disinfectant system comprises a chamber and a plurality of ultraviolet light emitting bulbs. The chamber may have at least one wall transparent to ultraviolet light and defining a treatment flow path for liquid to be treated with the ultraviolet light. The plurality of ultraviolet light emitting bulbs may be positioned external to the chamber, adjacent to the transparent wall to direct ultraviolet light into the chamber along the treatment flow path. The system may further include an inflow port, outflow port, and pump. The inflow port may be configured for passage the liquid to be treated into the treatment flow path. The outflow port may be configured for passage the treated liquid from the treatment flow path to an outlet of the chamber. The pump may be configured for pumping the liquid through the chamber. The system may further include a static mixer positioned in the chamber and comprising a plurality of vanes extending into the treatment flow path, dimensioned to impede laminar flow along the treatment flow path. The treatment flow path may include a gap passing between at least one of the vanes and the transparent wall.

In one embodiment, the chamber is defined between an outer wall of an inner tube and an inner wall of an outer tube, and wherein the outer tube comprises the transparent wall. The vanes may extend from the outer wall of the inner tube. The gap may be defined between the vanes and the inner wall of the outer tube. The vanes may spiral around a circumference of the inner tube. In one configuration, the vanes do not extend completely around a circumference of the inner tube. At least one vane may extend around the circumference of the inner tube between about 160 degrees and about 200 degrees. The vanes may be aligned along the length of the treatment flow path. The vanes may be spaced apart between about two feet and about three feet along the treatment flow path. Turbulence features may be located on a surface of at least one of the vanes to increase local turbulence. The turbulence features may comprise raised bumps along an interface of the inner tube and the vane. In still another aspect, a UV disinfectant system comprises a chamber and a plurality of ultraviolet light emitting bulbs. The chamber may have at least one wall transparent to ultraviolet light and defining a treatment flow path for liquid to be treated with the ultraviolet light. The plurality of ultraviolet light emitting bulbs may be positioned external to the chamber, adjacent to the transparent wall to direct ultraviolet light into the chamber along the treatment flow path. The system may further include an inflow port, outflow port, and pump. The inflow port may be configured for passage the liquid to be treated into the treatment flow path. The outflow port may be configured for passage the treated liquid from the treatment flow path to an outlet of the chamber. The pump may be configured for pumping the liquid through the chamber. The system may further include a static mixer positioned in the chamber and comprising a plurality of vanes extending into the treatment flow path, dimensioned to impede laminar flow along the treatment flow path. The system may further include a cabinet housing the chamber and bulbs and having an upper end and a lower end. A first blower may be positioned to drive airflow out of the cabinet at the lower end. A second blower may be positioned to drive airflow out of the cabinet at the upper end. A vent may enable airflow into the cabinet between the upper end and the lower end of the cabinet.

The first blower and the second blower may be variable speed blowers. The system may further comprise a temperature sensor to measure an air temperature in the cabinet. The first blower and second blower may be operationally coupled to the temperatures sensor such that the speed of the first blower and the second blower increase in response to a measured temperature above a set point temperature. The first blower and second blower may be operationally coupled to the temperatures sensor such that the speed of the first blower and the second blower decrease in response to a measured temperature below a set point temperature. The temperature sensor may comprise a thermocouple. The first blower may be located in the lower end of the cabinet and the second blower may be located in the upper end of the cabinet. The first blower may be positioned to drive airflow out of the cabinet at the lower end in a first direction and the second blower may be positioned to drive airflow out of the cabinet at the upper end in a second direction, and wherein the first direction is opposite the first direction. The vent may comprise a plurality of louvers.

In yet another aspect, a UV disinfectant system comprises a chamber and a plurality of ultraviolet light emitting bulbs. The chamber may have at least one wall transparent to ultraviolet light and defining a treatment flow path for liquid to be treated with the ultraviolet light. The plurality of ultraviolet light emitting bulbs may be positioned external to the chamber, adjacent to the transparent wall to direct ultraviolet light into the chamber along the treatment flow path. The system may further include an inflow port, outflow port, and pump. The inflow port may be configured for passage the liquid to be treated into the treatment flow path. The outflow port may be configured for passage the treated liquid from the treatment flow path to an outlet of the chamber. The pump may be configured for pumping the liquid through the chamber. The system may further include a static mixer positioned in the chamber and comprising a plurality of vanes extending into the treatment flow path, dimensioned to impede laminar flow along the treatment flow path. The system may further include a cabinet housing the chamber and bulbs.

An air temperature sensor may be configured to measure air temperature at one or more locations within the cabinet. A liquid temperature sensor may be configured to measure a liquid temperature at one or more locations within the chamber. A flow meter may be configured to measure a flow rate of liquid at one or more locations within the chamber. The system may further include a controller operable to control operations of the pump, bulbs, and blowers and operationally coupled to the air temperature sensor, liquid temperature sensor, and flow meter to receive collected measurement data. The controller comprises a processor, a computer-readable storage medium having instructions stored executable by the processor to perform the operations of the UV disinfectant system, and a user interface operable to interface users with the controller to view measurement data collected from the air temperature sensor, liquid temperature sensor, and flow meter and to modify at least one of power delivery to the bulbs, blower speed, or pump speed.

In one embodiment, the instructions stored in the computer-readable medium comprise a plurality of set point conditions defining preferred operational conditions comprising at least one of (a) an air temperature at the one or more locations in the cabinet, (b) a liquid temperature at the one or more locations within the chamber, (c) a flow rate at the one or more locations within the chamber, or (d) an illumination of the bulbs. The instructions stored in the computer-readable medium mat further include instructions to modify an operation of the UV disinfectant system in response to a non-conforming set point condition. The computer-readable storage medium may include additional instructions stored to modify an operation of the UV disinfectant system in response to a non-conforming set point condition which result in the operations comprising terminating power to the bulbs when at least one of (a) the flow meter measures no flow, (b) the air temperature sensor measures an air temperature higher than an air temperature set point, (c) the liquid temperature sensor measures a liquid temperature higher than a liquid temperature set point, or (d) the air temperature sensor measures an air temperature lower than an air temperature set point. The computer-readable storage medium may include additional instructions stored to modify an operation of the UV disinfectant system in response to a non-conforming set point condition which result in the operations comprising at least one of terminating power to pump or reducing pump speed when the liquid temperature sensor measures a liquid temperature below a liquid temperature set point, or supplying power to the pump or increasing speed of the pump when the liquid temperature sensor measures a liquid temperature above a liquid temperature set point. The computer-readable storage medium may store additional instructions stored to modify an operation of the UV disinfectant system in response to a non-conforming set point condition which result in the operations comprising supplying power to the blowers or increasing speed of the blowers when the air temperature sensor measures an air temperature above an air temperature set point. In one embodiment, the system further comprises a control panel associated with the cabinet, wherein the user interface comprises a local user interface provided on the control panel. The user interface may comprise a remote user interface accessible to a remote user device over a network, wherein the remote user interface is accessible by the remote user device to view measurement data, and wherein the remote user interface is operable by the remote user device to control an operation of the UV disinfectant system comprising at least one of (a) modifying power delivery to the bulbs to turn on or turn off the bulbs, (b) changing a speed of operation of the pump to modify a flow rate or temperature of the liquid pumped through the chamber, or (c) changing a speed of one or more blowers to modify air temperature at one or more locations within the cabinet. The computer-readable storage medium may store additional instructions which when executed by the processor keeps track of an operational life of the bulbs.

Embodiments of the present invention may be adapted for use with systems to apply antimicrobial solution to food items, for example, raw chicken, to disinfect the antimicrobial solution before it is recycled for reuse within the application system. Examples of aspects of such antimicrobial application systems are found in, for example, U.S. patent application Ser. Nos. 10/535,030; 14/471,846; 14/510,385; and Ser. No. 14/510,439, the contents of each of which are incorporated herein in their entirety.

BRIEF DESCRIPTION OF THE DRAWINGS

The above brief description, as well as further objects, features and advantages will be more fully appreciated by reference to the following detailed description taken in conjunction with the accompanying drawings, wherein.

DESCRIPTION

Figure 1:
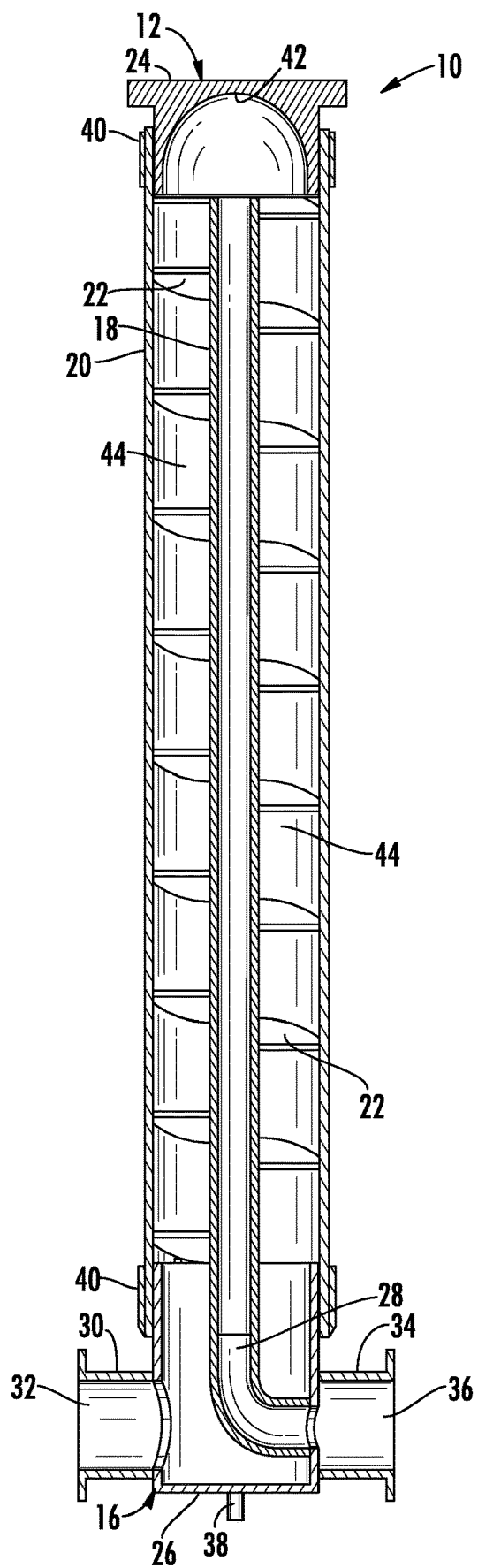
FIG. 1 is a sectional, side elevation view of a treatment chamber forming part of a radiation treatment device for use in a UV disinfectant system according to various embodiments.

Referring to FIG. 1, the reference numeral 10 refers in general to a radiation treatment device. The device 10 comprises a treatment chamber 12 and a radiation source 14 disposed in close proximity thereto, shown in FIG. 4. The treatment chamber 12 comprises a header 16, inner and outer tubes 18 and 20, a static mixer 22, and an end cap 24. The header 16 has an outer housing 26, an inner header tube 28, an input pipe 30 with an input opening 32, and an output pipe 34 with an output opening 36. The outer housing 26 is open at the top, closed at the bottom, and has two side openings disposed on opposite sides, with one side opening being larger than the other. A mount 38 is secured to the bottom wall of the outer housing 26. The input pipe is affixed to the outer housing 26, aligned with the larger of the two side openings. The output pipe 34 is affixed to the outer housing 26 aligned with the smaller of the two other side openings. The input and output pipes 30 and 34 both have inner diameters of approximately 1.5 inches. The inner diameter of the output pipe 34 is larger than the diameter of the side opening. The inner header tube 28 has an input opening centrally disposed and coaxially aligned with the outer housing 26 and an output opening aligned with the smaller of the two side openings. The inner diameter of the inner header tube 28 is substantially the same as the diameter of this side opening. The header 16 is preferably made of stainless steel and is of clean in place construction. It is of course understood that the header 16 may be made of any number of different materials or combinations of materials. It is also understood that the header 16 may be assembled or fabricated from a number of different parts or may be cast or molded as one or more integral pieces.

The outer tube 20 is made of a material that is transparent to UV radiation or to the type of radiation used. The outer tube 20 is preferably constructed of a polymer, is more preferably constructed of a fluoropolymer, and is most preferably constructed of fluorinated ethylene propylene. The outer tube may of course be constructed of any number of materials known to possess the desired degree of transparency. The outer tube 20 has a length of approximately 60 inches and has an inner diameter of approximately 1.25 inches. A lower portion of the outer tube 20 is secured to the header 16, such as by using a hose clamp 40. The end cap 24 is affixed to an upper portion of the outer tube 20, such as by using a hose clamp 40. A lower surface 42 of the end cap 24 is curved to assist in redirection of the liquid with minimal pressure drop. The cap 24 is preferably stainless steel.

An output end of the inner tube 18 is affixed to the input end of the inner header tube 28, and the inner tube 18 extends coaxially aligned within the outer tube 20 along most if not all of the height, or longitudinal length, of the outer tube 20. The inner tube 18 is preferably stainless steel having an inner diameter of substantially within a range of from approximately 0.5 inch to approximately 3.25 inch. The inner tube has an outer diameter that is substantially within a range of approximately from approximately 0.75 inch to approximately 3.5 inch. The outer diameter of the inner tube 18 and the inner diameter of the outer tube 20 are preferably selected to provide a relatively narrow annulus 44 between the two having a width of approximately 0.25 inch. An inner surface of the inner tube 18 defines an inner flow path.

An inner surface of outer tube 20 and an outer surface of inner tube 18 define an outer flow path. An opening in a distal end of the inner tube 18 places the outer flow path in fluid flow communication with the inner flow path. The outer surface of the inner tube 18 is not transparent with respect to the radiation from the radiation source 14 and is preferably reflective of the radiation.

The static mixer or helical member 22 is an auger style static mixer that is affixed to the outer diameter of the inner tube 18, such as by welding. The mixer 22 extends between the outer wall of the inner tube 18 and the inner wall of the outer tube 20 and preferably contacts the inner wall of the outer tube 20. The mixer 22 is preferably stainless steel.

Different degrees of winding may be used depending upon desired characteristics of the device 10. In one embodiment the winding provides a liquid travel path of approximately 3.9 inches for each 1 inch of annulus 44 height. For a treatment chamber 12 in which the height of the annulus 44 area is approximately 60 inches, this would provide a liquid travel path of approximately 234 inches.

Figure 2:
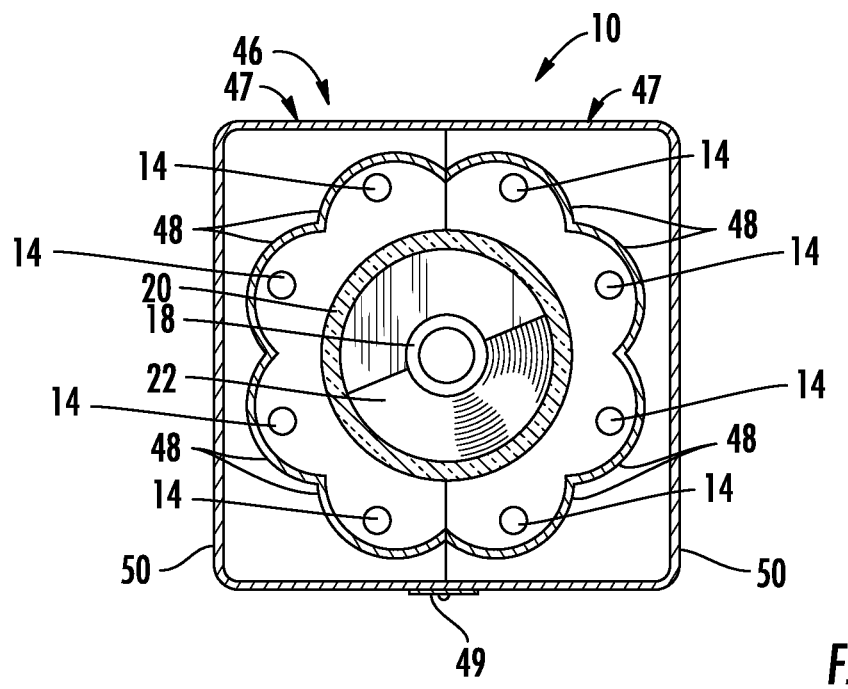
FIG. 2 is a sectional, overhead view of a radiation treatment device for use in a UV disinfectant system according to various embodiments.

Referring to FIG. 2, a modular illumination unit 46 is provided, formed from two mirror image sections 47. The sections 47 are connected to one another by a hinge 49 or in any conventional manner. Each section 47 comprises a plurality of bulbs 14, one or more reflectors 48, and a bracket 50. The bracket 50 supports and aligns the bulbs 14 and supports and aligns the reflector or reflectors 48 positioned adjacent to the bulbs 14. The reflector 48 is configured with a curved portion or segment, such as a semi-circular, hyperbolic, or parabolic shaped portion or segment, associated with each bulb 14, disposed and aligned to reflect and focus radiation emitted from outer portions of the bulb 14 back toward the treatment chamber 12. The segments are disposed so that the reflector 48 is generally clamshell shaped. In that regard, a cross section of one segment falling in a common plane of a cross section of an adjoining segment does not form a portion of a common circle or semi-circle with the cross section of the adjoining segment, Each cross section is preferably semi-circular, and each cross section of a segment has an arc length that is greater than approximately 45°. The inner surface of the reflector 48 is selected to be highly reflective of the radiation used. For example, if a UV bulb 14 is used, the inner surface is preferably polished aluminum. Each section 47 is secured to its mating section 47 and is secured within the cabinet 66 in any number of ways, such as being secured to a back wall of the cabinet or to brackets disposed within the cabinet 66. In the embodiment shown, one section 47 is disposed toward a back portion of the cabinet 66, and a mating section 47 is disposed toward a front portion of the cabinet 66 so that the front section 47 may be easily opened to provide access to the treatment chamber 12 and to the sections 47 of the illumination unit 46. Each section 47 is independently removable without the need to remove an associated treatment chamber or mated section 47. The brackets 50 of each section 47 are disposed to place the bulbs 14 in very close proximity to the outer surface of the outer tube 20. In the embodiment shown, in which the modular concept is used, a separate modular illumination unit 46 is associated with each treatment chamber 12. An extra or spare modular illumination unit 46 may be provided along with the device 10. This will reduce down time by making it easy to quickly replace an installed unit 46 with a spare unit 46 if the installed unit is in need of repair, maintenance, or replacement.

Figure 3:
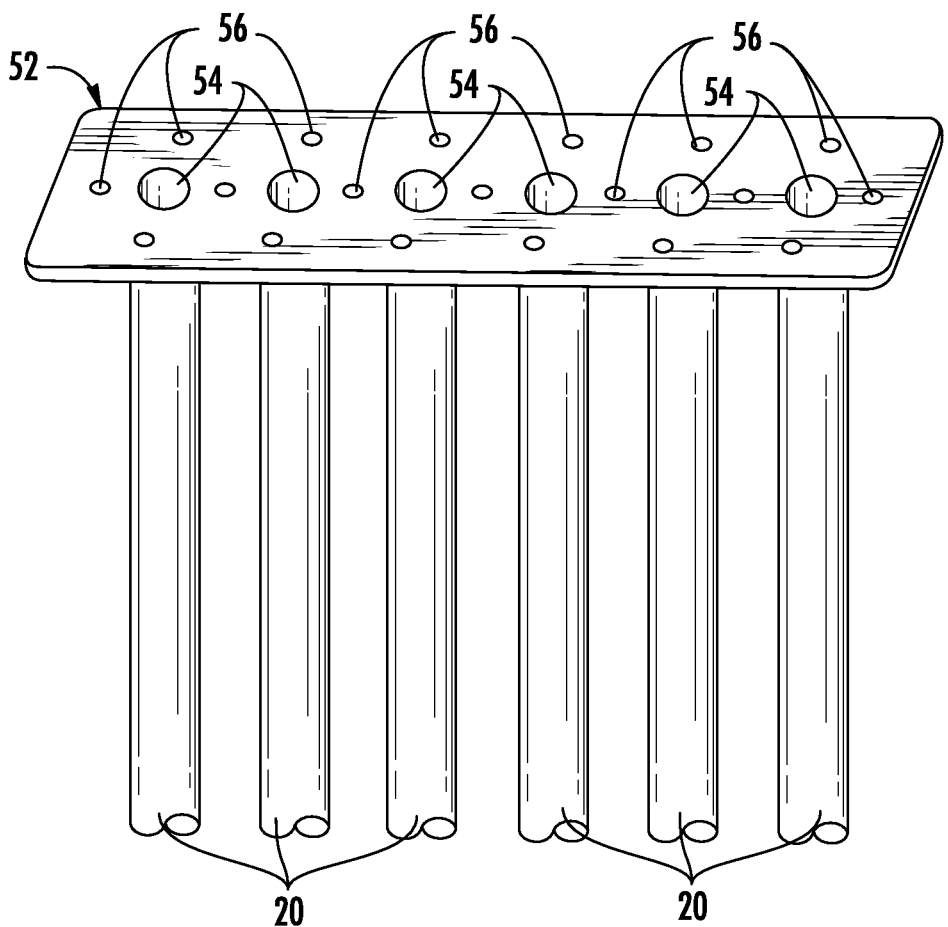
FIG. 3 is a partial, side elevation view of an alternate embodiment of a radiation treatment device for use in a UV disinfectant system according to various embodiments.
Figure 4:
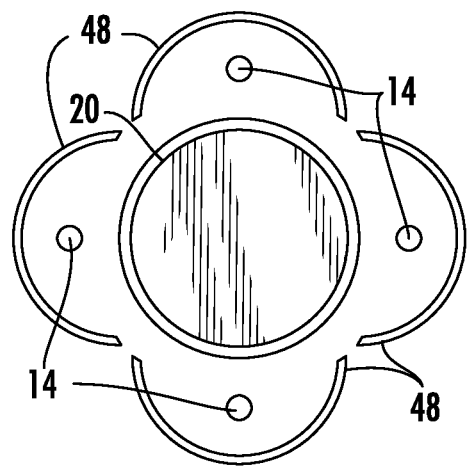
FIG. 4 is a is a partial, sectional, overhead view of an alternate embodiment of a radiation treatment device for use in a UV disinfectant system according to various embodiments.

In an alternate embodiment depicted in FIGS. 3 & 4, one or more bulb racks 52 may be used to support and align a plurality of outer tubes 20 of a plurality of treatment chambers 12, along with the bulbs 14 and reflectors 48 to be used with each treatment device 10. As seen in FIG. 3, sets of holes or openings 54 and 56 are provided to support and align the outer tubes 20 and bulbs 14, respectively.

Figure 5:
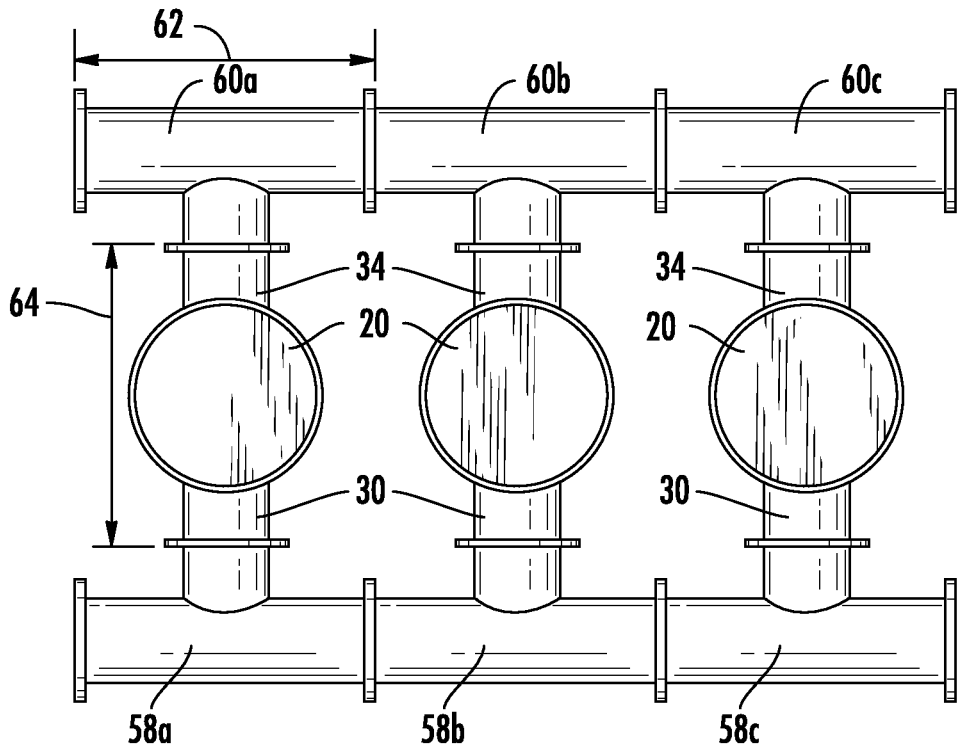
FIG. 5 is an overhead, perspective view of a parallel flow alignment of a radiation treatment device for use in a UV disinfectant system according to various embodiments.

Referring to FIG. 5, input and output manifolds 58 and 60 are provided and are disposed to allow for parallel flow of a liquid through a plurality of adjacent treatment chambers 12. The manifolds are provided in a modular arrangement with a first set of associated input and output manifold segments 58a and 60a, a second set of associated input and output manifold segments 58b and 60b, and so on for the desired number of treatment chambers 12 to be used. The length 62 of the each input and output manifold 58,60 segment is equal to the distance 64 between the input opening 32 of the input pipe 30 and the output opening 36 of the output pipe 34. This allows each treatment chamber 12 to be quickly and easily adjusted to provide for either parallel flow as seen in FIG. 5 or to provide for series flow as seen in FIG. 6.

Figure 6:
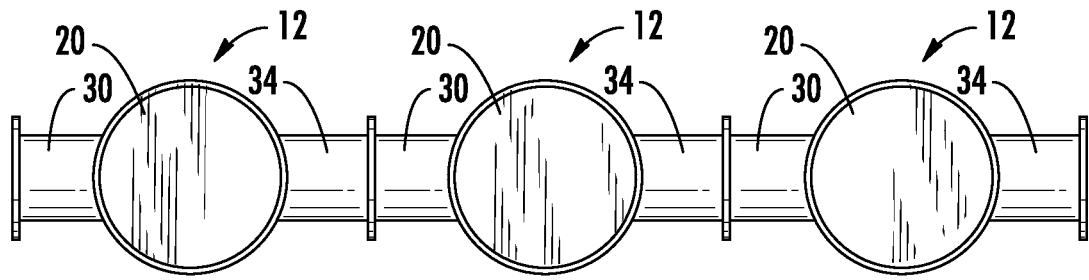
FIG. 6 is an overhead, perspective view of a series flow alignment of a radiation treatment device for use in a UV disinfectant system according to various embodiments.

FIG. 6 shows a plurality of treatment chambers 12 arranged to provide for series flow through a plurality of treatment chambers 12. In this arrangement, the output opening 36 of an output pipe 34 of a first treatment chamber 12 is aligned with an input opening 32 of an input pipe 30 of a second treatment chamber 12, and so on for the desired number of treatment chambers 12.

Figure 7:
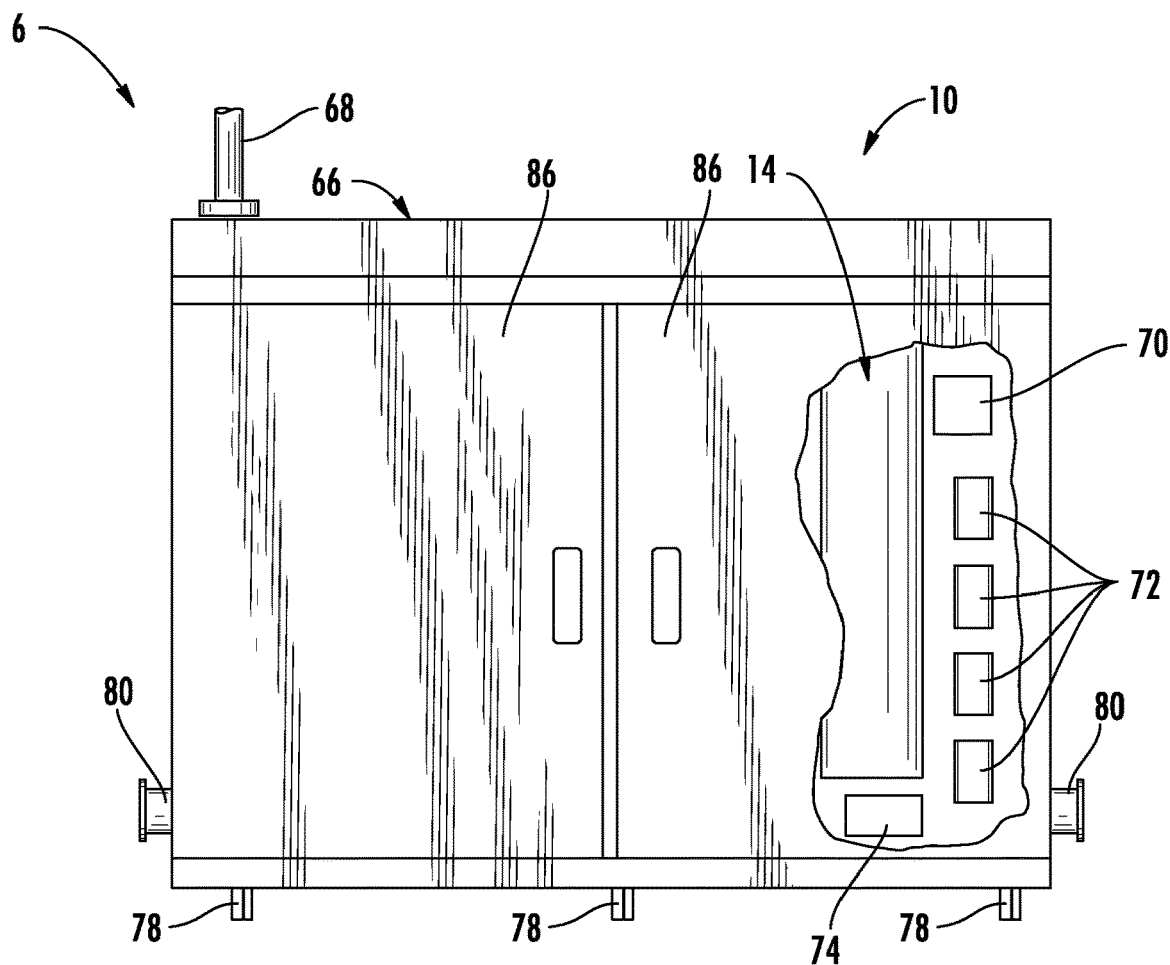
FIG. 7 is a front elevation view of a cabinet for housing a radiation treatment device for use in a UV disinfectant system according to various embodiments.

As shown in FIG. 7, a UV disinfectant system 6 may include a radiation treatment device 10 positioned in a cabinet 66 and including related components. One or more treatment chambers 12 and sets of associated bulbs 14, reflectors 48, and input and output manifolds 58,60 are housed within the cabinet 66. The cabinet 66 is preferably made primarily of stainless steel. Other components may be disposed within or positioned near the cabinet 66. For example, a power line 68 may supply power to controls 70 and to ballast 72 associated with each bulb 14, which may be housed in the cabinet 66 or separately above the cabinet 66. A fan 74 may be provided for cooling the ballast 72 and controls 70, and drain pipes 78 may be provided in the cabinet 66 floor. In the embodiment shown, a separate fan 74 may be associated each modular illumination unit 46, with the fan 74 disposed to provide a positive pressure cabinet.

Figure 8:
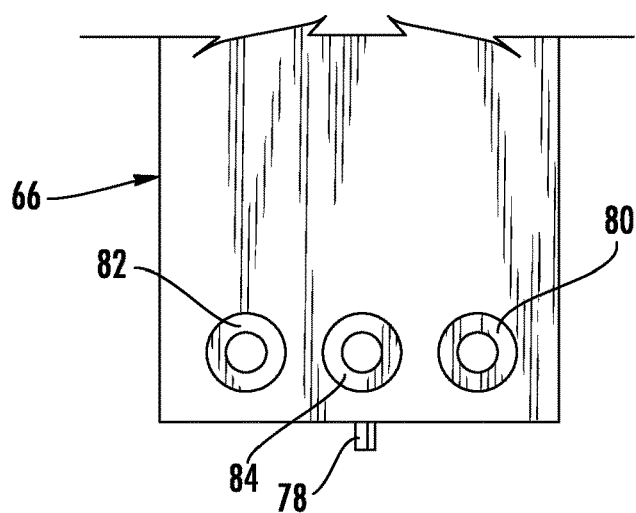
FIG. 8 is a partial, side elevation view of a cabinet for housing a radiation treatment device for use in a UV disinfectant system according to various embodiments.

It is of course understood that any number of different fan 74 arrangements may be used and that one or more fans may be disposed to provide either a positive pressure cabinet or a negative pressure cabinet. One or more input or output pipes 80, 82, and 84 may be provided, disposed in lower side walls of the cabinet 66. As best seen in FIG. 8, outer pipes 80 and 82 are disposed to align with input and output manifolds 58 and 60, respectively, to provide a path for parallel flow of liquid through the treatment chambers 12 such as when the treatment chambers 12 are aligned as depicted in FIG. 5. The centrally located pipes 84 are disposed to align with input and output pipes 30 and 34 of the treatment chambers 12 when the treatment chambers 12 are aligned for series flow, such as seen in FIG. 6.

Referring to FIGS. 5 & 6, in operation, a plurality of treatment chambers 12 are aligned as desired to provide for parallel or series flow through the desired number of treatment chambers 12. It is of course understood that a single treatment chamber 12 may also be used if desired. Once the treatment chambers 12 are aligned as desired and the cabinet doors 86 closed for added protection against exposure to UV radiation, the bulbs 14 are activated to provide UV radiation. The liquid to be treated is then provided to the device 10 at the desired pressure and flow rate. It is understood that the device 10 may be used in connection with most any liquid, including but not limited to clear or opaque liquids such as water, including wastewater, juices, brines, marinades, beverages, and the like.

In parallel flow (FIG. 5) the liquid will pass through and fill the desired number of input manifold segments 58a, 58b, 58c and will pass from each input manifold 58 segment into an associated treatment chamber 12. As best seen in FIG. 1, the liquid passes through the input pipe 30, through the housing 26, and into the annulus 44 between the inner tube 18 and outer tube 20. The static mixer 22 routes the liquid in a tight spiral pattern along a helical path upward through the annulus 44 to an upper portion of the treatment chamber 12. As the liquid passes through the narrow annulus 44 in close proximity to the bulbs 14, UV radiation from the bulbs 14 provides the desired degree of disinfection. The use of the auger style static mixer 22 provides for significant mixing and churning of the liquid as it passes upward through the annulus 44 so that different portions of the liquid are constantly being moved closer to and further from the bulbs 14. This ensures thorough and even radiation exposure throughout the liquid and greatly reduces the chances of leaving isolated portions relatively untreated or significantly over-treated. The end cap 24 arrests upward flow of the liquid and redirects the liquid to flow downward through the inner tube 18. The liquid then passes through the inner tube 18, through the inner header tube 28, and through the output pipe 34.

If the treatment chamber 12 is aligned to provide for parallel flow (FIG. 5), the liquid passes from the output pipe 34 to and through the associated output manifold 60 segment for further use or treatment. If the treatment chamber 12 is aligned to provide for series flow (FIG. 6), the liquid passes from the output pipe 34 of one treatment chamber 12 to the input pipe 30 of another treatment chamber 12 to repeat the process described above.

The rugged device 10 may be operated under wide ranges or pressures and flow rates without fear of damaging the device 10. For example, the device 10 may be safely operated at a working pressure reaching or exceeding a pressure that is preferably substantially within a range of from approximately 30 psig to approximately 60 psig and that is more preferably approximately 57 psig. The device 10 may withstand burst pressures reaching or exceeding a pressure that is preferably substantially within a range of from approximately 100 psig to approximately 300 psig and that is more preferably approximately 286 psig. Desired flow rates for many applications will typically be within a range of from approximately 1 gallon per minute to approximately 20 gallons per minute. Similarly, desired flow rates for typical clean in place cleaning will typically be less than or equal to approximately 25 gallons per minute. Still, much higher flow rates may be desirable for some applications, such as for the batch processing of juice. In the batch processing of juice, it is sometimes desirable to process flow rates reaching or exceeding approximately 70 gallons per minute. The system 6 may be configured to safely process flows rates of up to approximately 30 gallons per minute, up to approximately 55 gallons per minute, or approximately 80 gallons per minute. A treatment chamber 12 typically processes approximately 10 to 12 gallons per minute. Parallel flow is typically used for higher rates.

Other modifications, changes and substitutions are intended in the foregoing, and in some instances, some features will be employed without a corresponding use of other features. For example, any number of treatment chambers 12 may be used, from one to several. Similarly, a configuration of eight bulbs 14 per treatment chamber 12 may be used, but any number of bulbs 14 may be used in connection with a treatment chamber 12, from one to several. Also, any number of different types of mixers 22 may be used in the annulus 44, or a mixer 22 may be omitted. Further, any number of different flow paths may be used, including but not limited to a flow path that is roughly the reverse of that described above. Similarly, strictly series flow may be used, strictly parallel flow may be used, or any number of combinations of series and parallel flows may be used. Also, the header 16 may be disposed in different locations, such as at the top of the treatment chamber 12. Similarly, any number of different methods may be used to route the liquid to or from the annulus 44 area and to or from the inner tube 18. Although bulbs 14 providing UV radiation are preferred, any number of different types of radiation and types of radiation sources 14 may be used depending upon the desired application. Further, the reflectors 48 may take any number of shapes, sizes or configurations or may be omitted.

Figure 9A:
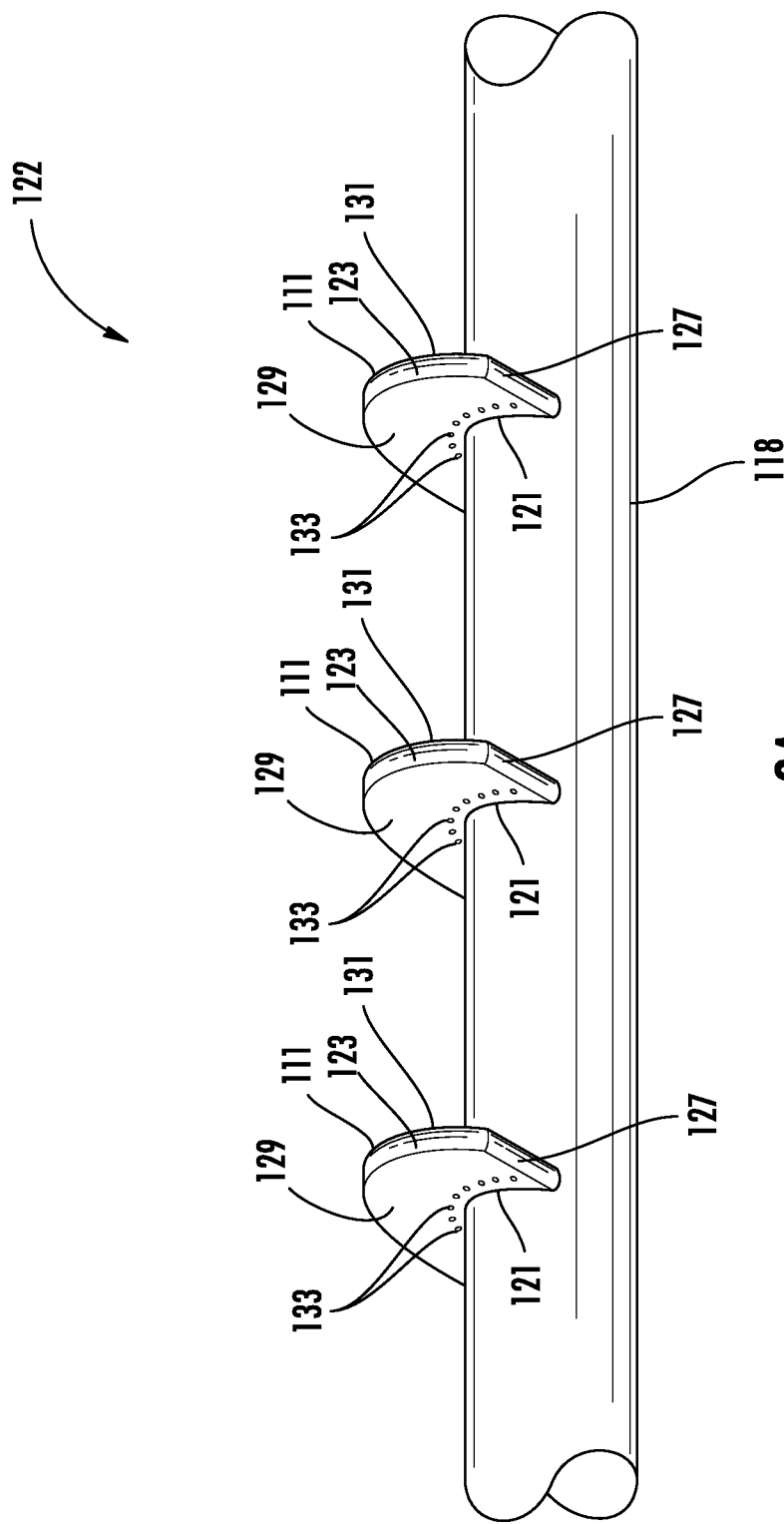
FIG. 9A is an overhead, perspective view of a stationary mixer of a radiation treatment device of a UV disinfectant system according to various embodiments.
Figure 10A:
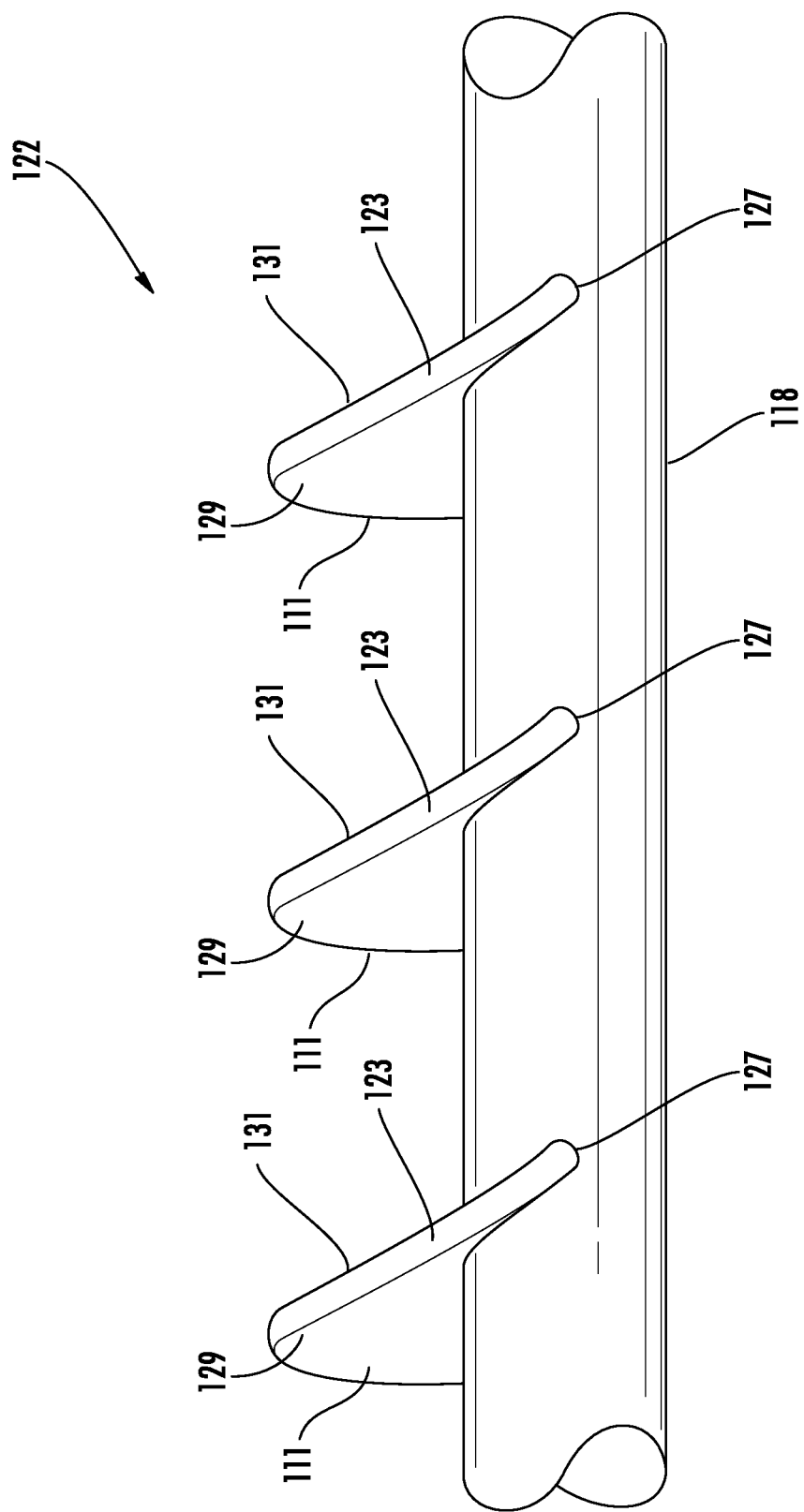
FIG. 10A is an overhead, perspective view of a stationary mixer of a radiation treatment device of a UV disinfectant system according to various embodiments.
Figure 10B:
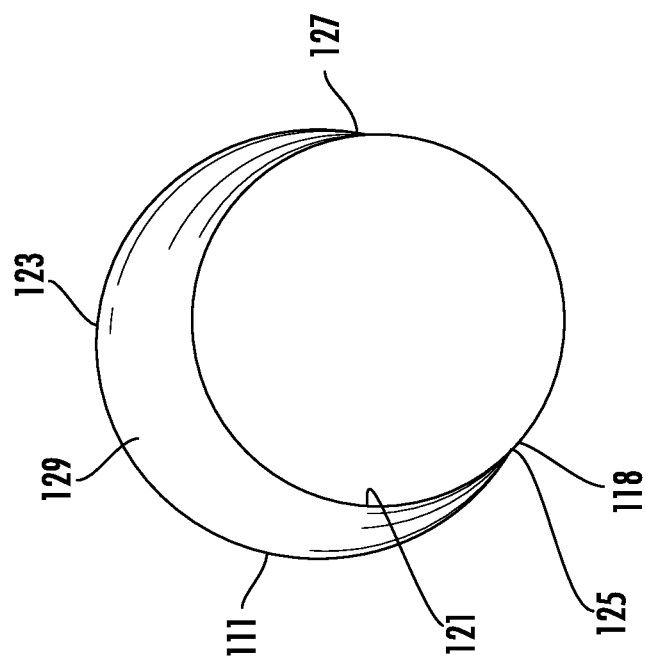
FIG. 10B is a axial, perspective view of the stationary mixer shown in FIG. 10A according to various embodiments.
Figure 9B:
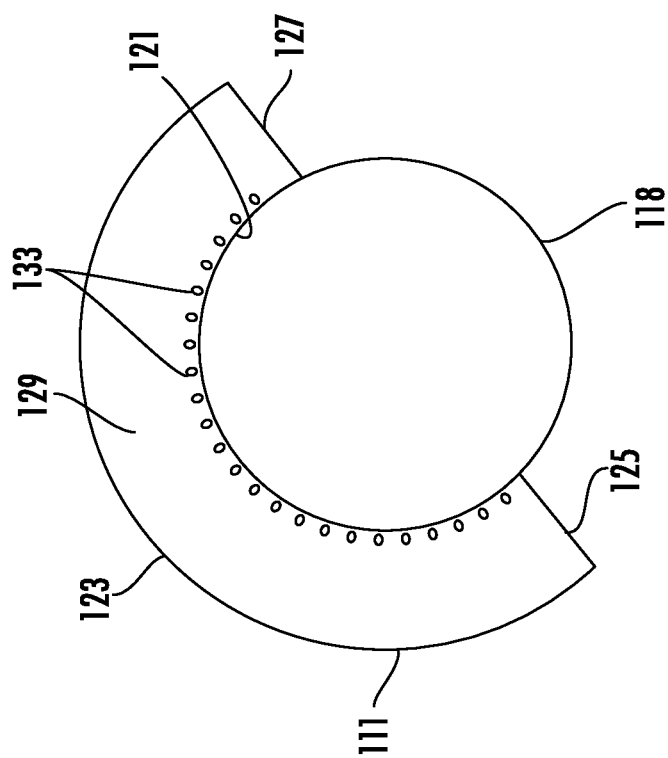
FIG. 9B is a axial, perspective view of the stationary mixer shown in FIG. 9A according to various embodiments.
Figure 11:
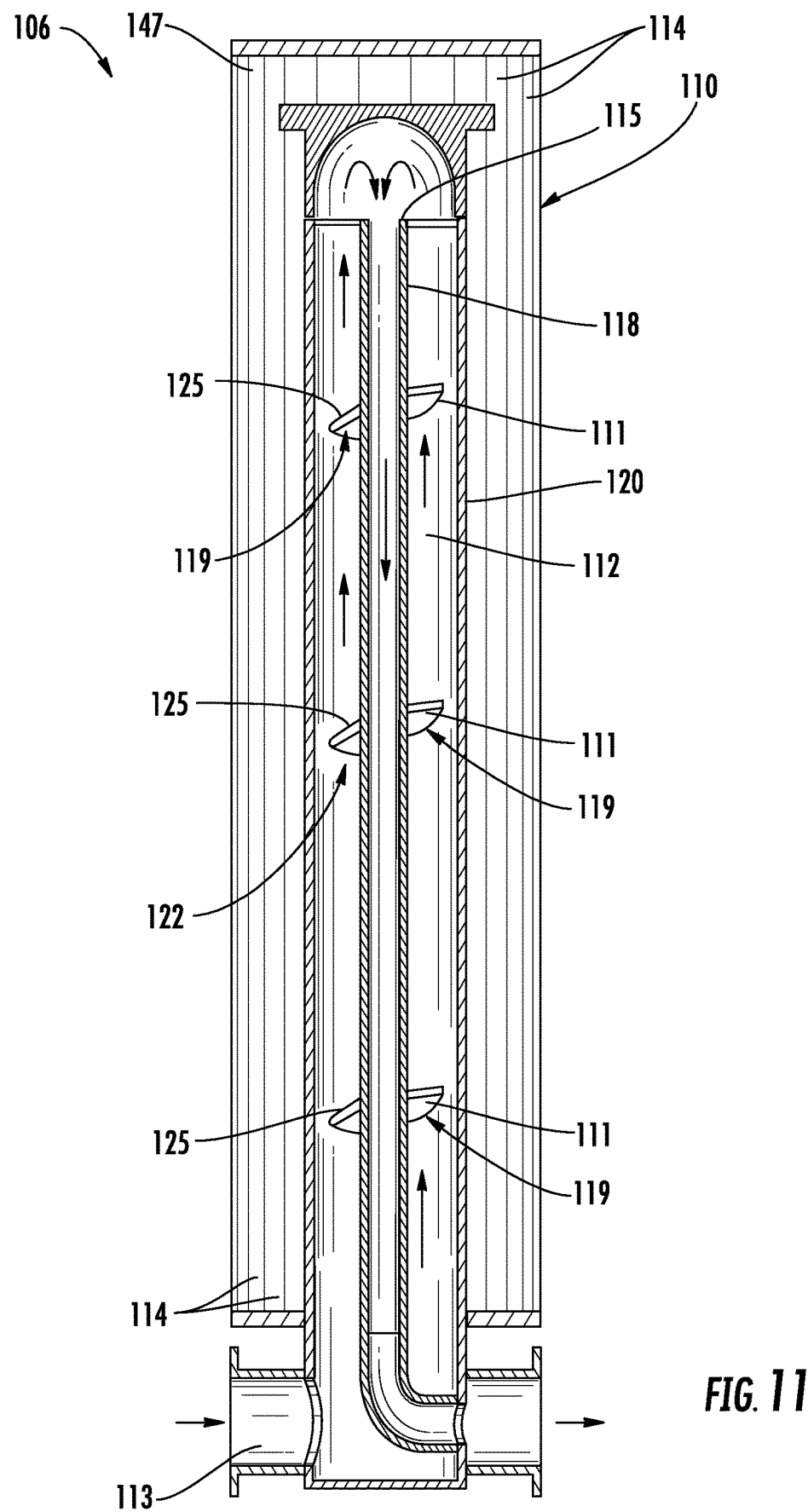
FIG. 11 is a partial, sectional, overhead view of a mixer and bulbs of a radiation treatment device of a UV disinfectant system according to various embodiments.
Figure 12A:
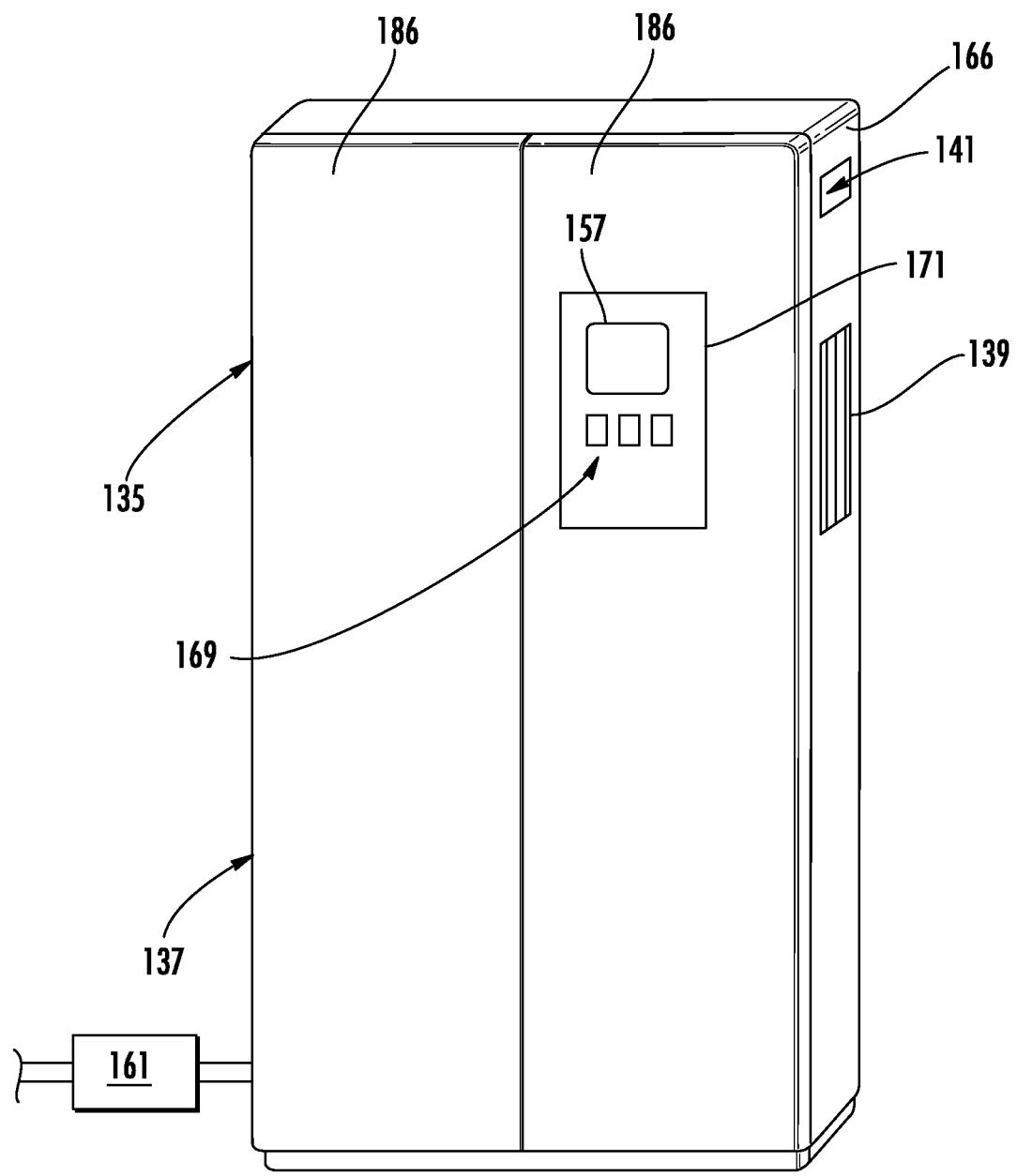
FIG. 12A is a front elevation view of a cabinet for housing a radiation treatment device of a UV disinfectant system according to various embodiments.
Figure 12B:
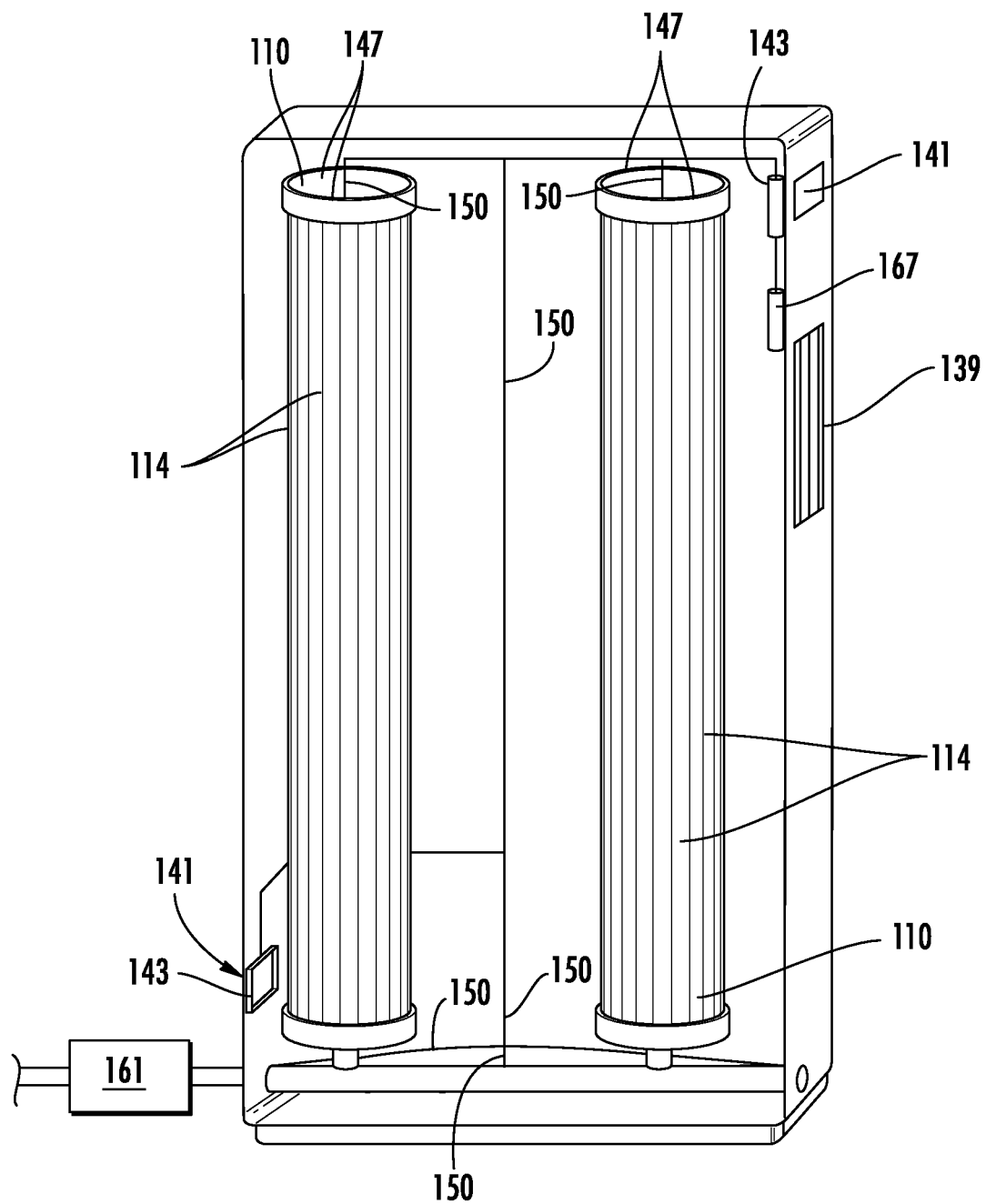
FIG. 12B is a front elevation view of the cabinet shown in FIG. 12A with the door removed according to various embodiments.
Figure 13:
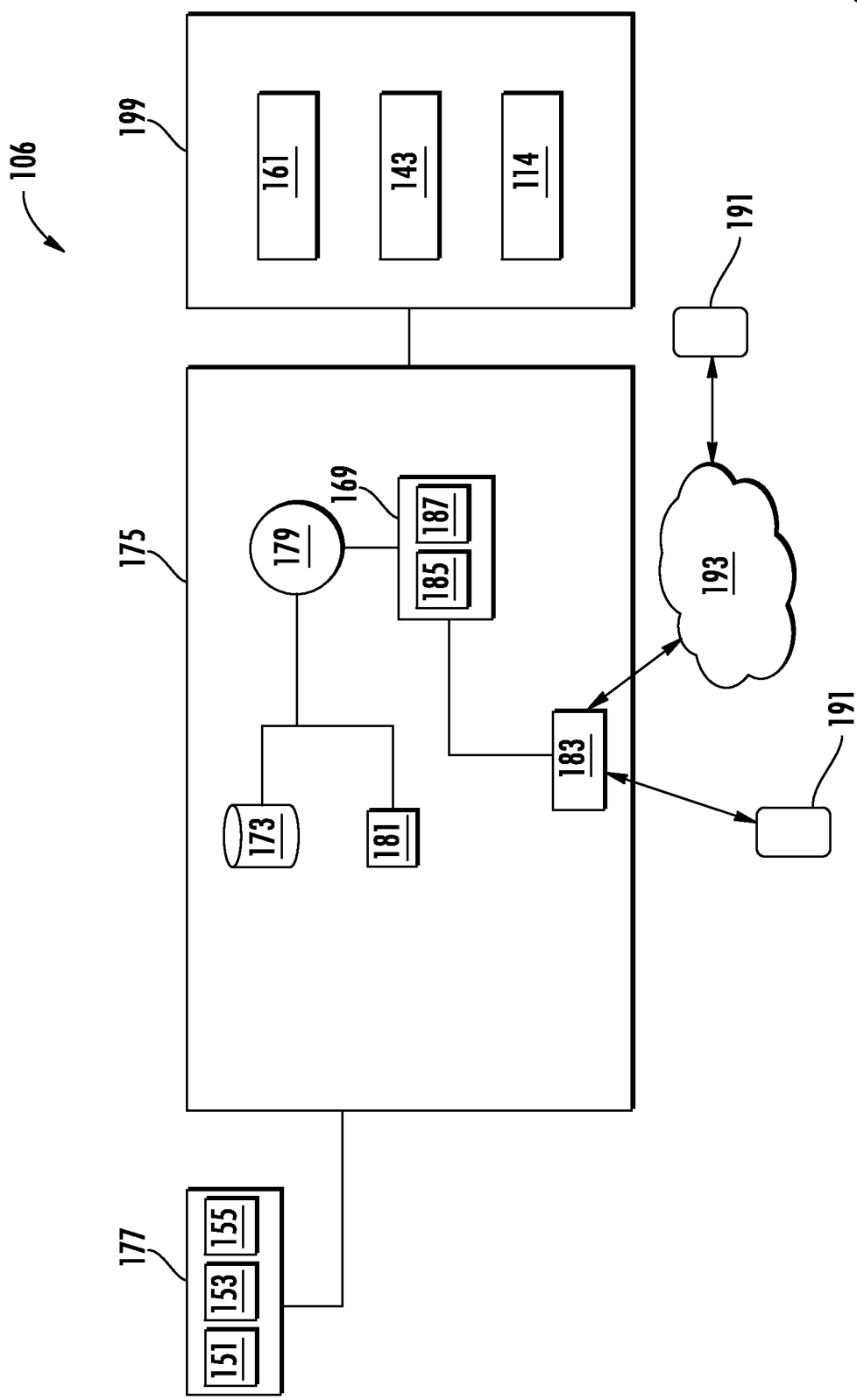
FIG. 13 schematically illustrates a control system of a UV disinfectant system according to various embodiments.

FIGS. 9A & 9B and FIGS. 10A & 10B illustrate additional embodiments of a static mixer 122 of a treatment device 110 for use with a UV disinfectant system 106 (see, e.g., FIGS. 11-13). Elevated views are shown in FIGS. 9A & 10A. Axial views are shown in FIGS. 9B & 10B. The static mixer 122 may include dimensions similar to those described above as modified below with respect to the static mixer 22. The static mixer 122 may be positioned within a treatment chamber 112 adjacent to a flow path of liquid through the chamber 112, an example of which is illustrated in FIG. 11 (arrows).

The static mixer 122 may be structured to create turbulence in liquid flow thereby mixing, e.g., turning over, churning, circulating, or otherwise agitating the liquid to thereby impede laminar flow. The static mixer 122 comprises extensions, referred to herein as vanes 111, located along the outer surface of the inner tube 118. The vanes 111 are positioned along the flow path and are dimensioned to create turbulence by impeding a direct flow of liquid through the treatment chamber 112. In particular, the vanes 111 are dimensioned to create turbulence along the flow path to prevent laminar flow. Thus, when liquid flows along the flow path between the inner tube 118 and outer tube 120, the liquid may be exposed to UV light that shines through a transparent portion of the outer tube 120 and into the flow path between the inner tube 118 and the outer tube 120 to act on the flowing liquid. For example, the vanes 111 may be dimensioned to create eddies of circulating liquid to disrupt laminar flow and to increase the proportion of the liquid that passes near the inner surface of the outer tube 120. The intensity of the UV light drops as the UV light passes through more liquid. So the intensity is greatest, and the disinfecting effect is greatest, closest to the inner surface of the outer tube 120. The rate at which the UV light intensity drops as it passes through the liquid may vary depending on factors such as light intensity, liquid composition or transparency/turbidity, outer tube composition or transparency, flow rate, etc.

The vanes 111 shown in FIGS. 9A & 9B and FIGS. 10A & 10B comprise a plurality of vanes 111 positioned along the height, or longitudinal length, of the inner tube 118 and extend axially into the flow path between the inner tube 118 and outer tube 120 to thereby agitate the liquid as it flows there along under the bulbs 114. The vanes 111 are preferably formed from materials resistant to corrosion, such as stainless steel, plastics, etc. The inner tube 118 may be formed of materials resistant to corrosion, such as stainless steel, plastics, etc., which may be the same or a different material than the vanes 111.

The vanes 111 extend axially from the inner tube 118 into the flow path between an inner axial end 121 and an outer axial end 123. The vanes 111 extend axially into the flow path toward the outer tube 120 but do not extend to the inner surface of the outer tube 120. Rather, a gap 119 is provided between the outer axial end 123 and the inner surface of the outer tube 120 to create greater turbulence. In other embodiments, the vanes 111 may extend axially to the inner surface of the outer tube 120. The vanes 111 further extend a circumferential distance around the inner tube 118 between a first circumferential end 125 and a second circumferential end 127. A first face 129 and a second face 131 are positioned between the inner axial end 121 and the outer axial end 123 and the first circumferential end 125 and the second circumferential end 127. The vanes 111 may be tilted, e.g., sideways, or spiraled and extend about half-way around the circumference of the inner tube 118. In other embodiments, the inner tube 118 may not be a tube, but may be a surface within the chamber 112 that is not a part of a separate tube with respect to another wall, e.g., the outer tube 120. For example, the flow path may be defined along a single tube or continuous arrangement of walls about the perimeter of the flow path. The vanes 111 may extend into the flow path from a first portion of the wall toward a second portion of the wall such that a gap is formed between the vanes 111 and the second portion of the wall. In one embodiment, the second portion of the wall is transparent to UV light.

The vanes 111 in the embodiments illustrated in FIGS. 9A & 9B and FIGS. 10A & 10B extend circumferentially around the inner tube 118 about 180°. In other embodiments, the static mixer may include one or more vanes 111 that extend less than 180° around the inner tube 118, such as between 180° and 135°, between 180° and 90°, between 180° and 45°, between 135° and 90°, between 135° and 45°, between 90° and 45°, or about 170°, about 160°, about 150°, about 140°, about 130, about 120°, about 120°, about 110°, about 100°, about 90°, about 80°, about 70°, about 60°, about 50°, about 40°, about 30°, about 20°, or about 10. In some embodiments, the static mixer may include one or more vanes 111 that extend greater than 180° around the inner tube 118, such as between 360° and 315°, between 360° and 270°, between 360° and 225°, between 360° and 180°, between 315° and 270°, between 315° and 225°, or about 360°, about 370, about 350°, about 340°, about 330°, about 320, about 310°, about 300°, about 290°, about 280°, about 270, about 260°, about 250°, about 240°, about 230°, about 220°, about 210, about 200°, or about 190°.

The vanes 111 may be aligned such that each is positioned along a corresponding circumferential portion of the inner tube 118, as shown in the embodiments illustrated in FIGS. 9A & 9B and FIGS. 10A & 10B. In other embodiments. The vanes 111 may be offset such that the vanes 111 occupy different circumferential portions of the inner tube 118, which may overlap along one or more portions of vanes 111 along the longitudinal length of the inner tube 118. The vanes 111 may be progressively offset such that a first vane 111 is positioned along a first circumferential length of the inner tube 118, a second vane 111 is positioned along a second circumferential length of the inner tube 118, adjacent to the first with respect to the circumference of the inner tube 118, and a third vane 111 is positioned along a third circumferential length of the inner tube 118, adjacent to the second with respect to the circumference of the inner tube 118. The vanes 111 may similarly be offset in a staggered formation with respect to the circumference and longitudinal length of the inner tube 118.

The embodiments illustrated in FIGS. 9A & 9B and FIGS. 10A & 10B comprise mixers 122 including three vanes 111. However, in other embodiments, any number of vanes 111 may be used. For example, fewer or additional vanes 111 may be includes such as two vanes 111, four vanes 11, five vanes 111, six vanes 111, or more. The vanes 111 may be spaced apart with respect to the longitudinal length of the inner tube 118. For example, the vanes 111 may be spaced apart between one foot and ten foot, one foot and six foot, one foot and three foot, two foot and six foot, two foot and three foot, or other distance. The spacing may be equivalent, as shown, or the vanes 111 may be bunched or concentrated along a longitudinal length of the inner tube 118 relative to one or more other longitudinal lengths of the inner tube 118. The vanes 111 illustrated also include similar dimensions; however, in some embodiments, the dimensions of a first vane 111 may be less than the dimensions of a second vane 111 or a second vane 111 and third vane 111.

The vanes 111 transverse a portion of the flow path adjacent to the inner tube 118 thereby impeding laminar flow or otherwise creating turbulence. The first face 129 is positioned at a non-perpendicular angle with respect to the direction of flow. In other embodiments, the first face 129 may be positioned perpendicular to the direction of flow. In the embodiment illustrated in FIGS. 9A & 9B, the first face 129 presents a substantially straight angle surface. In some embodiments, the first face 129 may present a concave or convex surface to impede laminar flow, as illustrated in FIGS. 10A & 10B. As shown in the embodiment illustrated in FIGS. 9A & 9B the first face 129 forms an angle with the outer surface of the inner tube 118 that is about 90° or greater. In the embodiment illustrated in FIGS. 10A & 10B, the first face 129 forms an angle with the outer surface of the inner tube 118 that is less than 90° along all or a portion of the circumferential length of the vane. In other embodiments, the first face 129 may form an angle with the outer surface of the inner tube 118 that is less than 90° along a first portion of the circumferential length of the vane 111 and greater than 90° along a second portion of the circumferential length of the vane 111. The first face 129 of the vanes 111 shown in FIGS. 10A & 10B include a substantially smooth surface extending from the inner axial end 121 to the outer axial end 123. In other embodiments, the first face 129 or the second face 131 may include additional turbulence features, such as bumps, divots, slots, pits, one or more grooves or groove patterns, or other turbulence producing feature. In the embodiment illustrated in FIGS. 9A & 9B, the surface of the first faces 129 include turbulence features comprising a plurality of raised bumps 133. The bumps 133 may be positioned adjacent to or along the interface between the first face 129 and the outer surface of the inner tube 118. The bumps 133 may be formed by any suitable method. For example, the bumps 133 may be formed by tack welds. In the illustrated embodiments, the second face 131 is positioned at a non-perpendicular angle with respect to the direction of flow. In other embodiments, the second face 131 may be positioned at a perpendicular angle with respect to the direction of flow. The second face 131 may include a substantially flat angle surface, as shown in FIGS. 9A & 9B, or include a concave or convex surface, as shown in FIGS. 10A & 10B. The second face 131 shown in FIGS. 9A & 9B form an angle with the outer surface of the inner tube 118 that is about 90° or less. In other embodiments, the second face 131 may form an angle with the outer surface of the inner tube 118 that is greater than 90° along all or a portion of the circumferential length of the vane, such in the embodiment illustrated in FIGS. 10A & 10B. In another embodiment, the second face 131 may form an angle with the outer surface of the inner tube 118 that is greater than 90° along a first portion of the circumferential length of the vane 111 and less than 90° along a second portion of the circumferential length of the vane 111. The surface of the second face 131 may further include turbulence features such as bumps, divots, slots, pits, one or more grooves or groove patterns, or other turbulence producing feature. The bumps may be positioned adjacent to or along the interface between the second face and the outer surface of the inner tube 118. The bumps may be formed by tack welds, for example.

The thickness of the vanes 111 in the embodiments illustrated in FIGS. 9A & 9B and FIGS. 10A & 10B are about the same from the inner axial end 121 to the outer axial end 123. In other embodiments, the thickness may increase from the inner axial end 121 to the outer axial end 123. In one embodiment, the thickness decreases from the inner axial end 121 to the outer axial end 123.

The thickness of the vanes 111 in the embodiments illustrated in FIGS. 9A & 9B and FIGS. 10A & 10B are about the same from the first circumferential end 125 to the second circumferential end 127. In other embodiments, the thickness may increase or decrease from the first circumferential end 125 to the second circumferential end 127.

The first circumferential end 125 and the second circumferential end 127 of the vanes 111 shown in the illustrated embodiment of FIGS. 10A & 10B taper toward the inner tube 118. In other embodiments, one or both of the first circumferential end and second circumferential end do not taper. For example, the vanes 111 shown in the embodiment illustrated in FIGS. 9A & 9B include defined circumferential ends 125, 127 that extend to the inner tube 128. In one embodiment, a portion of the outer axial end 123 extends axially outward a greater distance than another portion of the outer axial end 123. For example, a portion of the outer axial end 123 adjacent the first circumferential end 125 may extend a greater distance axially than a portion of the outer axial end 123 adjacent the second circumferential end 127 or along a central portion of the vane 111. The first circumferential end 125 adjacent to the outer axial end 123 may extend a same, greater, or lesser circumferential length than the first circumferential end 125 adjacent to the inner axial end 121. The first circumferential end 125 or the second circumferential end 127 may extend axially outward from the inner tube 118 a greater distance than a central portion of the vane 111 along the outer axial end 123.

FIG. 11 illustrates a UV disinfectant system 106 comprising a treatment device 110, shown in a sectional view, wherein the static mixer 122 is positioned in a chamber 112 and surrounded by a radiation section 147 comprising a plurality of radiation emitting bulbs 114, shown as comprising UV bulbs. An additional radiation section may be positioned over the illustrated radiation section 147 to encapsulate or surround the chamber 112 with UV radiation. The radiation sections 143 may be hinged such that two may be separated by pivoting of the hinge along one side to access the chamber 112 or bulbs 114. The arrows indicate direction of liquid flow through the chamber 112. Liquid to be treated is pumped into the chamber through inflow port 113. The liquid is then flowed along the treatment flow path defined between the walls of the chamber 112. The vanes 11 of the static mixer 122 impede laminar flow along the flow path. A gap 119 may be formed between the vane 111 and the adjacent wall of the chamber 112 within the flow path. The gap 119 may be defined between the vane 111 and the transparent portion of the chamber wall. As shown, the gap 119 is defined between the outer axial end 123 of the vane 111 and the chamber wall formed by the inner surface of the outer tube 120. The static mixer 122 is shown positioned in a treatment chamber 112 having walls comprising coaxially aligned inner 118 and outer tubes 120; however, other arrangements may be used according to various embodiments. For example, the static mixer 122 may comprise vanes 111 extending from the outer tube 120 toward the inner tube 118. Gaps 119 may similarly be formed therebetween.

FIG. 12A illustrates a UV disinfectant system 106 comprising a cabinet 166 according to various embodiments. FIG. 12B illustrates a view of the system 106 with the doors 186 removed. The cabinet 166 houses one or more treatment devices 10, 110 of the treatment system 106.

The system 106 may include sensors (not shown) configured to sense operational conditions. Sensor wiring 150 is shown in FIG. 12B; however, in some embodiments, one or more sensors may transmit or receive operation data wirelessly. Referring to FIG. 13 providing a schematic illustration of one embodiment of the system 106, the sensors may include one or more air temperature sensors 151 to measure air temperature within the cabinet 166. The sensors may also include one or more liquid temperature sensors 153 to measure liquid temperature within the chamber 112. The sensors may also include one or more flow meters 155 to measure flow rate of liquid pumped through the chamber 112 by one or more pumps 161.

Referring to FIGS. 12A-13, the system 196 may include blowers 143 are positioned to provide circulation or ventilation of the cabinet thereby dissipating heat build-up to prevent excessive air temperatures from damaging components of the system 106. Blowers 143 may include one or more fans, pumps, or other devices/structures configured to actively encourage air to flow from one location to another location. Blowers 143 may be positioned at the upper end 135 and lower end 137 of the cabinet 166. Ports 141 may extend through the cabinet 166 through which the blowers 143 urge air flow. Wiring 150 may operably couple the blowers 143 and sensors 151, 153, 155 with the controller 175. The wiring 150 may include a connection 167 to connect to the control panel 171.

The ports 141 and blowers 143 may be positioned with respect to the cabinet 166 to prevent cross circulation issues. In the illustrated embodiment, the system 106 includes two blowers 143 positioned at opposite corners of the cabinet 166, cattycorner across the box at opposite ends. In other embodiments, the ports 141 may be located at other sides of the upper and lower ends 135, 137 of the cabinet, such as along a back wall, the doors 186, or either the top or bottom wall. The blowers 143 may be positioned to blow air out of the cabinet 166. The blowers 143 may be located within the cabinet 166, as shown, or external to the cabinet 166. Additional ports 141 and blowers 143 may also be used along the upper end 135 and lower end 137 or, in one embodiment, along a middle portion of the cabinet. A vent 139 may extend into the cabinet 166 to provide ventilation. The vent 139 may be positioned along a wall of the cabinet 166. The vent 139 may be located along an upper end 135 of the cabinet 166, e.g., along a side wall or top of the cabinet 166, along a central portion of the cabinet 166 between the upper end 135 and lower end 133, or along the lower end 135 of the cabinet, e.g., along a lower side wall or bottom of the cabinet 166. The vent 139 may include louvers to allow the pressure within the interior of the cabinet 166 to equalize. Thus, air may move into the interior of the cabinet 166 through the vent 139 as air is moved out of the interior of the cabinet 166 by the action of the blowers 143. In one embodiment, an additional blower may be used with the vent 139. Multiple vents 139 may also be used. Blower ports 145 are formed through the cabinet 166 through which the blowers 143 may direct air. The blowers 143 may be positioned to move air out of the interior of the cabinet 166 from the lower end 137 and upper end 135, as shown, and the vent 139 may be located along a middle portion of the cabinet 166 to provide circulation of air through the interior of the cabinet 166 while avoiding cross circulation across the chamber walls.

The blowers 143 may comprise adjustable speed blowers 143. For example, the speed of the blower 143 may be adjusted to increase or decrease a speed of the blower 143. The speed may be adjusted by a switch. The switch may be operable by manual manipulation, e.g., by a user, at a location of the blower 143, which may be associated with the blower 143 or switchable at a user interface 169 of a control panel 171 or, in one embodiment, the switch may be operable remotely via an operation of a controller 175 comprising a user interface 169 accessible to monitor or control operations of the system 106 (see FIG. 13). The blower 143 may further comprise a variable frequency drive ("VFD") blower 143.

With further reference to FIG. 13, the system may further include a controller 175 to monitor or control operations of the system 106. The controller 175 may include one or more processors, servers, as well as databases, networks or network devices, and peripherals configured to obtain and transmit data and initiate control operations configured to perform in whole or in part the operations of the system 106. As shown, the controller 175 comprises a control module 107, e.g., one or more electronic data processors or central processing units having logic control functionalities. The controller 175 further comprises a memory unit comprising one or more computer readable data storage mediums, e.g., electronic data storage mediums such as recording media, read-only, volatile, non-volatile, semi-conductor based, or other data storage mediums known in the art. The computer readable storage medium, for example, includes one or more data storage mediums having stored thereon one or more programs or applications comprising software, firmware, or other instructions stored in one or more files executable by the processor of the control module to perform the various operations and functions of the controller 175. The instructions may include a monitoring program or operating system configured to monitor or control operations of the system 106 and interface users or access devices 191, which may include interaction with additional applications or service, with the system 106.

The controller 175 may be operationally associated with control and monitoring operational devices 199 such as actuators, valves, pumps, power switches, etc. for controlling or monitoring operational conditions of the UV disinfectant system 106. For example, the controller 175 may be operationally associated with pumps 161, blowers 143, and bulbs 114. The controller 175 may be configured to initiate or otherwise provide control instructions to the UV disinfectant system 106 to modulate operations in response to a determination, e.g., to maintain or address non-conforming set points.

As introduced above, the controller 175 includes a controller 175 configured to execute a monitoring program 120. The monitoring program 120 may include a web application, service, or bundled services in which various interfaces 169 such as local interfaces 187 or remote interfaces 185 may interface with the controller 175 and monitoring program. In various embodiments, a local interface 187 may include the control panel 171. Remote interfaces 185 may include access devices 191 programmed to remotely interface with the controller 175. In at least one embodiment, access devices 191 include a notification device configured to receive notifications from the controller 175. Remote interfaces 185 may interface with the controller 175 in a cloud platform environment. For example, the various services or applications may be executed in a cloud environment through interaction of the access devices 191 and controller 175.

The controller 175 includes a control module comprising a digital processor to route or make available the operation data collected to one or more computer readable storage mediums or interfaces. The storage medium, for example, may be accessed by the control module to retrieve, store, or archive operation data, which may include raw, processed, or analyzed operation data, events, as well as parameter definitions, including rules, statistics, tables, algorithms, or other data used to process or analyze data including generating or identifying operational conditions, as described in more detail below. For example, the storage medium may include files executable by the controller 175 to perform one or more aspects of the monitoring program. The controller 175 may be under the control of the monitoring program configured to interface the functionalities of the controller with users and access devices 191. The monitoring program may include set points, operational condition identifications, and analysis parameters, any of which may include customizable definitions to fit the desired application. For example, the controller 175 may be operatively associated with one or more processes of the UV disinfectant system 106 to monitor, collect, analyze, process, and/or communicate data indicative of operational conditions, events, or states as defined by the monitoring program. Example set points that may be defined in the system 106 may include a liquid temperature at the one or more locations within the chamber 112, a flow rate at the one or more locations within the chamber, or an illumination of the bulbs 114. When a set point is found to be non-conforming, e.g., at a threshold level indicating a control operation the controller 175 may modify an operation of the UV disinfectant system in response to the non-conforming set point condition. For example, the controller 175 may terminate power to the bulbs when the flow meter 155 measures no flow, the air temperature sensor 151 measures an air temperature higher than an air temperature set point, the liquid temperature sensor 153 measures a liquid temperature higher than a liquid temperature set point, or the air temperature sensor measures an air temperature lower than an air temperature set point. The controller 175 may also terminate power to pump 161 or reduce pump speed when the liquid temperature sensor 153 measures a liquid temperature below a liquid temperature set point, or supply power to the pump 161 or increasing speed of the pump 161 when the liquid temperature sensor 153 measures a liquid temperature above a liquid temperature set point. The controller 175 may also be programmed to supply power to the blowers 143 or increase speed of the blowers 143 when the air temperature sensor 151 measures an air temperature above an air temperature set point.

The system 106 may comprise one or more networks including networked devices, e.g., nodes or endpoints, configured to communicate via wired or wireless connections. Networks may comprise local, virtual, wide area, cloud/internet area, or internet-based aspects. The networks may include one or more distributed communication networks that may include virtual hardware, distributed databases, parallel or distributed computing schemes, service oriented application architectures, public, private, or hybrid clouds, open architectures or architectures utilizing web API, web applications, or mashups, and may employ client-server or peer-to-peer models. The controller 175 may also include a communication port 183 configured to transmit and receive data, which may be transmitted and received over a network. The communication port 183 may include one or more data ports, communication ports, transmitters, receivers, transceivers, network cards, modems, gateways, routers, switches, firewalls, local, virtual, wide area, cloud/internet area, or internet-based distributed networks, Ethernet, wireless or wired digital communication devices, telecommunication devices, monitors, speakers, lights, buttons, knobs, or peripherals. The controller 175 may include a wired or wireless data or communication port 183 into which a user may couple a local or remote user access device 191 such as a computer, tablet, notebook, smart phone, mobile communication device, programming card, flash drive, memory stick, or special purpose diagnostic, programming, or system administration device. For example, in one embodiment, the controller 175 includes a data port 181 configured to receive a data storage device such as a flash drive defining one or more set points, administrative parameters, or security definitions. In some embodiments, the communication port 183 of the control panel 171 provides an access point to user access devices 191 to access the monitoring program and its functionalities.

The controller 175 may include a user interface 169 comprising a control panel 171. The panel 171 may be a standalone unit for control of the device 110 and associated operations. The control panel 171 may receive operation data from the plurality of sensors 177, such as measurement data from air temperature sensors 151, liquid temperature sensors 153, and flow meter 155. The control panel 171 may include a graphical user interface 157 for displaying information related to the operation of the UV disinfectant system 106. The control panel 171 also comprises various peripherals such as selection devices and LED indicators. In one embodiment, the control panel 171 include a touch screen. The user interface 169 may be programmed to interface users with the operations of a monitoring program to view, define, or modify operation conditions or set points.

The control panel 171 may be located locally with respect to the cabinet 166 to provide users with a local access point to the controller 175. In various configurations, users may use the control panel 171 to update or modify set points or query the computer readable storage medium for operation data or analysis, e.g., to generate or define reports, view event logs, historical or projected performance, or real-time operation data or operational conditions or to initiate collection of real-time operation data. The control panel 171 may also allow users to access, define, or modify security features such as permissions or user access levels, perform administrative tasks, override automated operations, or initiate, terminate, or modify operations.

The graphical user interface 157 may include presentation of operation data. The graphical user interface 157 may also include a touch screen interface providing local interface 187 with the control panel 171. A user may access the control panel 171 locally, or remotely in some embodiments, to view the current state of multiple aspects of the UV disinfectant system in real-time. In one embodiment, the user may select one of the identified set points to view or change the values defining the current set points. Typically, it will be preferable to require the user to establish authorization, e.g., by providing an identification or authorization code, before allowing the user to modify certain or any set point definitions or values.

The control panel 171 may be provided on the outside of the cabinet 166 or another location associated with the cabinet 166. The graphical user interface 157 may include LED lights that indicate measurement data from the sensors. The control panel 171 may also be configured to track operational life of the bulbs 114, which may allow for efficient preventative maintenance, reducing downtime.

The user interface 169 may also include a remote user interface 185 accessible via a network 193. The network 193 may include a local or distributed network, for example. In one embodiment, the network 193 allows users to remotely access the controller 175 via an internet connection, which may include remote access to the outside control panel LED data. Once accessed by a remote access device 191, a user may remotely view operational data, such as measurement data, in real time. The access device 191 may be configured with an monitoring/control application or the user may provide an authorization code to access the operational data, e.g., current or historical operation data, control operations, or update or define checkpoints. For example, in some embodiments, users accessing the control panel 171 remotely via a remote access device 191 may access the control operations of the control panel 171 to, e.g., control power to bulbs 114, control power to or modulate speed of blowers 143, control power to or modulate speed of pumps 161. In one embodiment, a remote user access device 191 may modify power delivery to the bulbs to turn on or turn off the bulbs, changing a speed of operation of the pump 161 to modify a flow rate or temperature of the liquid pumped through the chamber, or changing a speed of one or more blowers to modify air temperature at one or more locations within the cabinet.

The controller 175 is configured to operatively associate with one or more sensors 177 positioned to sense, detect, or measure conditions of the UV disinfectant system 106 in real-time. The sensors 177 may include liquid temperature sensors 153, flow meters 155, or air temperature sensors 151, as described above with respect to FIGS. 12A & 12B. The sensors 177 may be positioned at one or more locations to detect and obtain operation data associated operational conditions. In various embodiments, the operation data associated with operational conditions may be communicated by the sensors 177, e.g., transmitted, relayed or routed to, or otherwise obtained by, to the controller 175 in real-time. Transmission of the operation data may be by any manner known in the art, e.g., via wired or wireless communication. For example, in one embodiment, sensors 177 may be configured to transmit operation data via a wired or wireless transmitter or transceiver configured to transmit the sensed operation data to the controller 175.

In one embodiment, the speed of the VFD blower 143 or adjustable speed blower 143 may be dynamically controlled by the operation of the sensors, e.g., via set points defined in the system 106. For example, the controller 175 may be configured with set points defining desired operational criteria with respect to air temperature, liquid temperature, liquid flow rates, power delivery, projected component operational life spans, service intervals, etc. When operational data collected by the sensors 177 or calculated by the controller 175 are determined to be non-conforming, e.g., outside of defined set points such as meeting a threshold difference in a set point value, the control panel 171 may be configured to take an action defined in the system 106. For example, the strength of the UV and effectiveness of the disinfection may be monitored by the system 106. In one implementation, the flow meter 155 and liquid temperature sensor 153 may be configured to provide data to the controller 175, which the controller 175 may compare to a programmed set point and thereafter terminate power to the bulbs 114 if flow is below a flow set point, e.g., reach a threshold value, such as no flow, or the liquid temperature is above a liquid temperature set point. Beneficially, turning off the bulbs 114 if there is no flow or if the temperature of the liquid gets too hot may prevent thermal damage to components of the system 106 that could otherwise bring down the whole system 106.

In various embodiments, a liquid temperature sensor 153 may comprise a thermocouple to measure the liquid temperature and may comprise a switch that turns off the pump 161 and power delivery to the bulbs 114 when temperature rises above a desired temperature. The thermocouple may be utilized to measure the liquid temperature within the chamber 112, which may be at one or more locations, e.g., at or adjacent to the inflow port, along the flow path, at or adjacent to the outflow port, along the inner pathway of the inner tube 118, or after the treated liquid has exited the chamber The thermocouple may operate in conjunction with the flow meter 155. The thermocouple temperature sensor may also be utilized to control the speed of the blowers 143, which may be VFD blowers 143. In one embodiment, an air temperature sensor 151 may comprise a thermocouple measurement device including a switch to modify operation of the system 106, e.g., terminate power to the bulbs 114 when temperature rises above a desired temperature, terminate power to blowers 143 or increase blower speed when temperature rises above a desired level, or terminate power to the pump 161 when temperature is below a desired temperature, such as when the bulbs 114 are not illuminated.

OTHER MATTERS

The foregoing description of various embodiments is provided to enable any person skilled in the art to make and use the present invention and its embodiments. Various modifications to these embodiments are possible, and the generic principles presented herein may be applied to other embodiments as well.

It will be apparent to one of ordinary skill in the art that some of the embodiments as described hereinabove may be implemented in many different embodiments of software, firmware, and hardware in the entities illustrated in the figures. The actual software code or specialized control hardware used to implement some of the present embodiments do not limit the present invention.

As used herein, a "computer" or "computer system" may be, for example and without limitation, either alone or in combination, a personal computer (PC), server-based computer, main frame, server, microcomputer, minicomputer, laptop, personal data assistant (PDA), cellular phone, pager, processor, including wireless and/or wireline varieties thereof, and/or any other computerized device capable of configuration for receiving, storing and/or processing data for standalone application and/or over a networked medium or media. For example, various embodiments may include access devices or be configured to communicate, e.g., transmit data or interface, with the controller and program as described herein.

Computers and computer systems described herein may include operatively associated computer-readable memory media such as memory for storing software applications and instructions used in obtaining, processing, storing and/or communicating data. It can be appreciated that such memory can be internal, external, remote or local with respect to its operatively associated computer or computer system. Memory may also include any means for storing software or other instructions including, for example and without limitation, a hard disk, an optical disk, floppy disk, DVD, compact disc, memory stick, ROM (read only memory), RAM (random access memory), PROM (programmable ROM), EEPROM (extended erasable PROM), and/or other like computer-readable media.

Some embodiments may be implemented, for example, using a machine-readable medium or article which may store an instruction or a set of instructions that, if executed by a machine, may cause the machine to perform a method and/or operations in accordance with the embodiments. Such a machine may include, for example, any suitable processing platform, computing platform, computing device, processing device, computing system, processing system, computer, processor, or the like, and may be implemented using any suitable combination of hardware and/or software. The machine-readable medium or article may include, for example, any suitable type of memory unit, memory device, memory article, memory medium, storage device, storage article, storage medium and/or storage unit, for example, memory, removable or non-removable media, erasable or non-erasable media, writeable or rewriteable media, digital or analog media, hard disk, floppy disk, Compact Disk Read Only Memory (CD-ROM), Compact Disk Recordable (CD-R), Compact Disk Rewriteable (CD-RW), optical disk, magnetic media, various types of Digital Versatile Disk (DVD), a tape, a cassette, or the like. The instructions may include any suitable type of code, such as source code, compiled code, interpreted code, executable code, static code, dynamic code, and the like. The instructions may be implemented using any suitable high-level, low-level, object-oriented, visual, compiled and/or interpreted programming language, such as C, C++, Java, BASIC, Perl, Matlab, Pascal, Visual BASIC, assembly language, machine code, and so forth. The embodiments are not limited in this context.

It can be appreciated that, in certain aspects, a single component may be replaced by multiple components, and multiple components may be replaced by a single component, to provide an element or structure or to perform a given function or functions. Except where such substitution would not be operative to practice certain embodiments, such substitution is considered within the scope.

The controller has been illustrated and described as comprising several separate functional elements, such as modules or units. Although certain of such modules or units may be described by way of example, it can be appreciated that a greater or lesser number of modules or units may be used and still fall within the scope of the embodiments. Further, although various embodiments may be described in terms of modules or units to facilitate description, such modules or units may be implemented by one or more hardware components (e.g., processors, DSPs, PLDs, ASICs, circuits, registers, servers, clients, network switches and routers), software components (e.g., programs, subroutines, logic) and/or combination thereof.

In various embodiments, the control system or application system, including antimicrobial application equipment, may comprise multiple modules connected by one or more communications media. Communications media generally may comprise any medium capable of carrying information signals. For example, communications media may comprise wired communications media, wireless communications media, or a combination of both, as desired for a given implementation. Examples of wired communications media may include a wire, cable, printed circuit board (PCB), backplane, semiconductor material, twisted-pair wire, co-axial cable, fiber optics, and so forth. An example of a wireless communications media may include portions of a wireless spectrum, such as the radio-frequency (RF) spectrum. The embodiments are not limited in this context.

The modules or units may comprise, or be implemented as, one or more systems, sub-systems, devices, components, circuits, logic, programs, or any combination thereof, as desired for a given set of design or performance constraints. For example, the modules may comprise electronic elements fabricated on a substrate. In various implementations, the electronic elements may be fabricated using silicon-based IC processes such as complementary metal oxide semiconductor (CMOS), bipolar, and bipolar CMOS (BiCMOS) processes, for example. The embodiments are not limited in this context.

Unless specifically stated otherwise, it may be appreciated that terms such as "processing", "generating", "calculating", "determining", "analyzing" or the like, refer to the action or processes of a computer or computing system, or similar electronic computing device, that manipulates or transforms data represented as physical quantities (e.g., electronic) within the computing system's registers or memories into other data similarly represented as physical quantities within the computing system's memories, registers or other such information storage, transmission or display devices. The embodiments are not limited in this context. An action such as "identifying" when performed by a computer or computer system may include identification by determining, accessing system data, comparisons with system data, instructions, or the like. An action such as initiating may include causing an event or thing initiated either directly or indirectly. For example, initiating may include signaling, providing power or instructions, physical manipulation, transmission of data, calculation of conditions, or other step resulting in the event sought to be initiated. Furthermore, an action such as "storing", when used in reference to a computer or computer system, refers to any suitable type of storing operation including, for example, storing a value to memory, storing a value to cache memory, storing a value to a processor register, and/or storing a value to a non-volatile data storage device.

Various embodiments are described and illustrated in this specification to provide an overall understanding of the composition, function, operation, and application of the disclosed system, apparatus and methods. It is understood that the various embodiments described and illustrated in this specification are non-limiting and non-exhaustive. Thus, the invention is not necessarily limited by the description of the various non-limiting and non-exhaustive embodiments disclosed in this specification. The features and characteristics illustrated or described in connection with various embodiments may be combined with the features and characteristics of other embodiments. Such modifications and variations are intended to be included within the scope of this specification. As such, the claims may be amended to recite any features or characteristics expressly or inherently described in, or otherwise expressly or inherently supported by, this specification. Further. Applicant reserves the right to amend the claims to affirmatively disclaim features or characteristics that may be present in the prior art.

Any patent, publication, or other disclosure material identified in this specification is incorporated by reference into this specification in its entirety unless otherwise indicated, but only to the extent that the incorporated material does not conflict with existing descriptions, definitions, statements, or other disclosure material expressly set forth in this specification. As such, and to the extent necessary, the express disclosure as set forth in this specification supersedes any conflicting material incorporated by reference into this specification. Any material, or portion thereof, that is said to be incorporated by reference into this specification, but which conflicts with existing definitions, statements, or other disclosure material set forth in this specification, is only incorporated to the extent that no conflict arises between that incorporated material and the existing disclosure material. Applicants reserve the right to amend this specification to expressly recite any subject matter, or portion thereof, incorporated by reference into this specification.

The matter set forth in the foregoing description and accompanying drawings is offered by way of illustration only and not as a limitation. While the systems, methods, compositions, and devices for recycling of antimicrobial treatment solution have been described and illustrated in connection with certain embodiments, many variations and modifications will be evident to those skilled in the art and may be made without departing from the spirit and scope of the disclosure. For example, the systems, methods, compositions, and devices disclosed herein have been identified, adapted to, and designed for food processing use, and particularly to processing of chicken and other poultry parts. Those having skill in the art will understand upon reading the present disclosure that the subject matter may be applied to other processing uses. The disclosure is thus not to be limited to the precise details of methodology or construction set forth above as such variations and modification are intended to be included within the scope of the disclosure.

What is claimed is:

1. A UV disinfectant system, the system comprising:
   a chamber having at least one wall transparent to ultraviolet light and defining a treatment flow path for liquid to be treated with the ultraviolet light, wherein the chamber is defined between an outer wall of an inner tube and an inner wall of an outer tube, the outer tube comprising the transparent wall;
   a plurality of ultraviolet light emitting bulbs positioned external to the chamber, adjacent to the transparent wall to direct ultraviolet light into the chamber along the treatment flow path;
   an inflow port for passage of the liquid to be treated into the treatment flow path;
   an outflow port for passage of the treated liquid from the treatment flow path to an outlet of the chamber;
   a pump for pumping the liquid through the chamber;
   a static mixer positioned in the chamber, the static mixer comprising
   a plurality of discontinuous and axially spaced vanes extending spirally around an outer circumferential portion of the inner tube or an inner circumferential portion of the outer tube and extending into the treatment flow path,
   wherein the static mixer is dimensioned to impede laminar flow along the treatment flow path,
   wherein the treatment flow path includes a gap passing between at least one of the vanes and the transparent wall; and
   wherein each vane has a first face and a second face opposite the first face,
   wherein
   along a first portion of the vane, the first face intersects the inner tube at an angle of less than 90 degrees with respect to a longitudinal axis of the inner tube, and
   along a second portion of the vane, the first face intersects the inner tube at an angle of greater than 90 degrees with respect to the longitudinal axis of the inner tube;
   a cabinet housing the chamber and bulbs, the cabinet having an upper end and a lower end;
   a first blower positioned to drive airflow out of the cabinet at the lower end;
   a second blower positioned to drive airflow out of the cabinet at the upper end; and
   at least one vent through the cabinet wall between the upper end and the lower end of the cabinet;
   an air temperature sensor to measure air temperature at one or more locations within the cabinet;

a liquid temperature sensor to measure a liquid temperature at one or more locations within the chamber;
a flow meter to measure a flow rate of liquid at one or more locations within the chamber; and
a controller operable to control operations of the pump, bulbs, and blowers and operationally coupled to the air temperature sensor, liquid temperature sensor, and flow meter to receive collected measurement data, the controller comprising:
a processor;
a non-transitory computer-readable storage medium having instructions stored executable by the processor to perform the operations of the UV disinfectant system; and
a user interface operable to interface users with the controller to view measurement data collected from the air temperature sensor, liquid temperature sensor, and flow meter and to modify at least one of power delivery to the bulbs, blower speed, or pump speed; and
wherein the plurality of discontinuous and axially spaced vanes comprises at least three vanes, wherein immediately adjacent vanes are not equally spaced apart along the treatment flow path.

2. A UV disinfectant system, the system comprising:
a chamber having at least one wall transparent to ultraviolet light and defining a treatment flow path for liquid to be treated with the ultraviolet light, wherein the chamber is defined between an outer wall of an inner tube and an inner wall of an outer tube, the outer tube comprising the transparent wall;
a plurality of ultraviolet light emitting bulbs positioned external to the chamber, adjacent to the transparent wall to direct ultraviolet light into the chamber along the treatment flow path;
an inflow port for passage of the liquid to be treated into the treatment flow path;
an outflow port for passage of the treated liquid from the treatment flow path to an outlet of the chamber;
a pump for pumping the liquid through the chamber; and
a static mixer positioned in the chamber, the static mixer comprising a plurality of discontinuous and axially spaced vanes extending spirally around an outer circumferential portion of the inner tube or an inner circumferential portion of the outer tube and extending into the treatment flow path,
wherein the static mixer is dimensioned to impede laminar flow along the treatment flow path,
wherein the treatment flow path includes a gap passing between at least one of the vanes and the transparent wall; and
wherein each vane has a first face and a second face opposite the first face,
wherein
along a first portion of the vane, the first face intersects the inner tube at an angle of less than 90 degrees with respect to a longitudinal axis of the inner tube, and
along a second portion of the vane, the first face intersects the inner tube at an angle of greater than 90 degrees with respect to the longitudinal axis of the inner tube; and
wherein the plurality of discontinuous and axially spaced vanes comprises at least three vanes, wherein immediately adjacent vanes are not equally spaced apart along the treatment flow path.

3. The system of claim 2, wherein the vanes extend around the outer circumference of the inner tube and wherein the gap is defined between the vanes and the inner wall of the outer tube.

4. The system of claim 2, wherein the vanes extend around the outer circumference of the inner tube or the inner circumference of the outer tube between about 160 degrees and about 200 degrees.

5. The system of claim 2, wherein the vanes are aligned along the length of the treatment flow path such that the vanes extend around corresponding circumferential portions of the inner tube.

6. The system of claim 2, wherein the vanes are axially spaced apart between about two feet and about three feet along the treatment flow path.

7. The system of claim 2, wherein turbulence features are located on at least one of the faces of at least one of the vanes to increase local turbulence.

8. The system of claim 7, wherein the turbulence features comprise raised bumps along an interface of the inner tube and the vane.

9. The system of claim 2, wherein the vanes are offset along the length of the treatment flow path such that the vanes extend around different circumferential portions of the inner tube.

10. The system of claim 2, wherein the static mixer comprises at least three vanes.

* * * * *

UNITED STATES PATENT AND TRADEMARK OFFICE
CERTIFICATE OF CORRECTION

PATENT NO. : 11,497,824 B2
APPLICATION NO. : 16/095715
DATED : November 15, 2022
INVENTOR(S) : Justin Massey and Tim Yeaman It is certified that error appears in the above-identified patent and that said Letters Patent is hereby corrected as shown below:

In the Specification

Column 5, Line 13, remove "is a" after "is a"
Column 5, Line 32, change "a" to --an--
Column 5, Line 37, change "a" to --an--
Column 7, Line 64, remove "the" after "of"
Column 8, Line 25, insert --with-- after "associated"
Column 11, Line 21, change "130" to --130°--
Column 11, Line 23, change "10" to --10°--
Column 11, Line 29, change "370" to --370°--
Column 11, Line 30, change "320" to --320°--
Column 11, Line 31, change "270" to --270°--
Column 11, Line 32, change "210" to --210°--
Column 11, Line 36, change "embodiments. The" to --embodiments, the--
Column 11, Line 56, change "includes" to --included--
Column 11, Line 56, change "four vanes 11" to --four vanes 111--
Column 13, Line 45, change "vanes 11" to --vanes 111--
Column 17, Line 24, change "include" to --includes--
Column 18, Line 3, change "an" to --a--
Column 21, Line 46, change "Further." to --Further,--

Signed and Sealed this
Ninth Day of May, 2023

Katherine Kelly Vidal
*Director of the United States Patent and Trademark Office*